US012275696B2

(12) United States Patent
Andrews et al.

(10) Patent No.: US 12,275,696 B2
(45) Date of Patent: *Apr. 15, 2025

(54) PROCESS FOR PREPARING TAPINAROF

(71) Applicant: Dermavant Sciences GmbH, Basel (CH)

(72) Inventors: Ian Paul Andrews, King of Prussia, PA (US); Nicholas Calandra, Cambridge, MA (US); Tyler Andrew Davis, Research Triangle Park, NC (US); Ravinder Reddy Sudini, King of Prussia, PA (US)

(73) Assignee: DERMAVANT SCIENCES GMBH, Basel (CH)

( * ) Notice: Subject to any disclaimer, the term of this patent is extended or adjusted under 35 U.S.C. 154(b) by 146 days.

This patent is subject to a terminal disclaimer.

(21) Appl. No.: 18/164,309

(22) Filed: Feb. 3, 2023

(65) Prior Publication Data

US 2023/0174445 A1 Jun. 8, 2023

Related U.S. Application Data

(63) Continuation of application No. 17/174,566, filed on Feb. 12, 2021, now Pat. No. 11,597,692, which is a continuation of application No. 16/849,346, filed on Apr. 15, 2020, now Pat. No. 10,961,175, which is a continuation of application No. 16/189,268, filed on Nov. 13, 2018, now Pat. No. 10,647,649.

(60) Provisional application No. 62/584,192, filed on Nov. 10, 2017.

(51) Int. Cl.
| | |
|---|---|
| C07C 39/08 | (2006.01) |
| A61K 31/05 | (2006.01) |
| C07C 37/00 | (2006.01) |
| C07C 37/07 | (2006.01) |
| C07C 45/54 | (2006.01) |
| C07C 45/63 | (2006.01) |
| C07C 45/72 | (2006.01) |
| C07C 50/24 | (2006.01) |
| C07C 51/09 | (2006.01) |
| C07C 51/38 | (2006.01) |
| C07C 59/353 | (2006.01) |
| C07C 67/03 | (2006.01) |
| C07C 67/293 | (2006.01) |
| C07C 67/343 | (2006.01) |
| C07C 69/716 | (2006.01) |

(52) U.S. Cl.
CPC ............ *C07C 39/08* (2013.01); *C07C 37/002* (2013.01); *C07C 37/07* (2013.01); *C07C 45/54* (2013.01); *C07C 45/63* (2013.01); *C07C 45/72* (2013.01); *C07C 50/24* (2013.01); *C07C 51/09* (2013.01); *C07C 51/38* (2013.01); *C07C 59/353* (2013.01); *C07C 67/03* (2013.01); *C07C 67/293* (2013.01); *C07C 67/343* (2013.01); *C07C 69/716* (2013.01); *A61K 31/05* (2013.01)

(58) Field of Classification Search
CPC ....... C07C 39/08; C07C 37/002; C07C 50/24; C07C 51/38; C07C 67/03; A61K 31/05
See application file for complete search history.

(56) References Cited

U.S. PATENT DOCUMENTS

| | | |
|---|---|---|
| 4,515,883 A | 5/1985 | Sasaki |
| 5,068,458 A | 11/1991 | Dales et al. |
| 5,268,517 A | 12/1993 | Kober et al. |
| 5,478,856 A | 12/1995 | Suzuki et al. |
| 5,589,506 A | 12/1996 | Hashimoto et al. |
| 5,760,277 A | 6/1998 | Naef et al. |
| 6,410,596 B1 | 6/2002 | Hopp et al. |
| 6,552,085 B2 | 4/2003 | Inman et al. |
| 6,624,197 B1 | 9/2003 | Nag et al. |
| 6,689,922 B1 | 2/2004 | Bernardon |
| 7,321,050 B2 | 1/2008 | Chen et al. |
| 7,868,047 B2 | 1/2011 | Chen et al. |
| 8,487,009 B2 | 7/2013 | Chen et al. |
| 9,308,239 B2 | 4/2016 | Thiboutot et al. |
| 10,195,160 B2 | 2/2019 | Sonti et al. |
| 10,376,475 B2 | 8/2019 | Cote-Sierra et al. |
| 10,426,743 B2 | 10/2019 | Sonti et al. |

(Continued)

FOREIGN PATENT DOCUMENTS

| | | |
|---|---|---|
| CA | 2266763 A1 | 10/1999 |
| CN | 101531571 A | 9/2009 |

(Continued)

OTHER PUBLICATIONS

Kronenwerth et al. Facile Synthesis of Cyclohexanediones and Dialkyiresorcinols—Bioactive Natural Products from Entomopathogenic Bacteria, Eur. J. Org. Chem. 8026-8028. (Year: 2014).*

Ali et al. "New Method for Isometization of (Z)-Stilbenes into the (E)-Isomers Catalyzed by Diaryl Disulfide" 1992, CA 118:233541, Chemical and Pharmaceutical Bulletin 40(10):3 Pages.

Ames et al. "Part III: Alkaline Hydrolysis of Ethyl 2:4-Dioxo-6-Styrylcyclohexanecarboxylate" 1958, Notes, J. Chemical Society 181:911-912.

Bezou et al. "Efficient Synthesis of p-Vinyl-Trans-Stilbene" Apr. 1996, Synthesis, 449-451.

(Continued)

Primary Examiner — Sikarl A Witherspoon
(74) Attorney, Agent, or Firm — DLA Piper LLP (US)

(57) ABSTRACT

The present invention provides processes for the preparation of 3, 5-Dihydroxy-4-isopropyl-trans-stilbene or a salt or solvate thereof and novel intermediates used therein. In some embodiments the 3, 5-Dihydroxy-4-isopropyl-trans-stilbene is prepared from (E)-2-chloro-2-isopropyl-5-styryl-cyclohexane-1,3-dione. Also disclosed are crystal forms of 3, 5-Dihydroxy-4-isopropyl-trans-stilbene or a salt or solvate thereof and pharmaceutical compositions comprising same.

18 Claims, 2 Drawing Sheets

(56) References Cited

U.S. PATENT DOCUMENTS

| | | | |
|---|---|---|---|
| 10,647,649 | B2 | 5/2020 | Andrews et al. |
| 10,961,175 | B2 | 3/2021 | Andrews et al. |
| 11,617,724 | B2 | 4/2023 | Sonti et al. |
| 2003/0073712 | A1 | 4/2003 | Wang et al. |
| 2011/0144212 | A1 | 6/2011 | Subbaraju et al. |

FOREIGN PATENT DOCUMENTS

| | | |
|---|---|---|
| CN | 101564537 B | 5/2011 |
| CN | 101648851 B | 10/2012 |
| CN | 103172497 A | 6/2013 |
| CN | 104003848 A | 8/2014 |
| CN | 103992212 B | 7/2015 |
| CN | 105884581 A | 8/2016 |
| CN | 201701915931.8 | 9/2017 |
| EP | 0170105 A2 | 2/1986 |
| EP | 0334119 B1 | 6/1993 |
| FR | 1442295 A | 6/1966 |
| GB | 1465661 A | 2/1977 |
| JP | S5721341 A | 2/1982 |
| JP | S58159410 A | 9/1983 |
| JP | H0753359 A | 2/1995 |
| JP | H1072330 A | 3/1998 |
| JP | 2001261585 A | 9/2001 |
| JP | 2009269910 A | 11/2009 |
| WO | 1992016486 A1 | 10/1992 |
| WO | 1999059561 A2 | 11/1999 |
| WO | 2001042231 A2 | 6/2001 |
| WO | 2004031117 A1 | 4/2004 |
| WO | 2019063002 A1 | 4/2019 |

OTHER PUBLICATIONS

Bissonnette et al. "Efficacy and Safety of Topical WBI-1001 in Patients with Mild to Moderate Psoriasis: Results from a Randomized Double-Blind Placebo-Controlled, Phase II Trial" 2012, J. European Academy of Dermatology and Venereology 26:1516-1521.

Bissonnette et al. "Efficacy and Safety of Topical WBI-1001 in Patients with Mild to Severe Atopic Dermatitis: Results from a 12-Week, Multicentre, Randomized, Placebo-Controlled Double-Blind Trial" 2012, British Association of Dermatologists 166:853-860.

Bissonnette et al. "Efficacy and Safety of Topical WBI-1001 in the Treatment of Atopic Dermatitis: Results From a Phase 2A, Randomized, Placebo-Controlled Clinical Trial" Apr. 2010, Reprinted in Archives of Dermatology 146(4):446-449.

Christensen et al. "Excelsaoctaphenol, A Stilbene Dimer From Chlorophora Excelsa" 1989, Phytochemistry Caplus 111:54148, 3 Pages.

Cushman et al. "Synthesis and Evaluation of Analogues of (Z)-1-(4-Methoxyphenyl)-2-(3,4,5-trimethoxyphenyl) ethene as Potential Cytotoxic and Antimitotic Agents" Jun. 26, 1992, J. Medicinal Chemistry 352293-2306.

Delle Monache et al. "Isolation and Structure of Longistylin A, B, C, D and Other New Prenylated Stilbenes From Lonchocarpus Violaceus" 1977, CA 87:117649, 2 Pages.

Dudek et al. "Synthesis of Ferrocenethiols Containing Oligo(phenylenevinylene) Bridges and Their Characterization on Gold Electrodes" 2001, J. American Chemical Society 123(33):8033-8038.

Eicher et al. "Synthese Von Bryophyten-Inhaltsstoffen 2. Synthesen von prenylierten Bibenzyl-Derivaten" 1991, Synthesis 30:98-102.

Erdtman et al. "Bromination Products of 3, 5-dimethoxystilbene" 1949, CAPLUS 43:4524, 02 Pages.

Fang et al. "Flavonoids and Stilbenes from Armand Pine" May 20, 1988, Phyto Chemistry 27(5):1395-1397.

Gao et al. "Preparation of Chitosan Microspheres Loading of 3,5-dihydroxy-4-i-propylstilbene and In Vitro Release" Jan. 6, 2011, J. Polymer Research 18:1501-1508.

International Search Report and Written Opinion for PCT/US2018/060749 dated Jan. 18, 2019, 08 Pages.

Joseph et al. "Improved Preparation of 2,5-Dimethyl-1,3-Cyclohexanedione" 1995, Organic Preparations and Procedures International 27(4):499-500, ISSN 0004613633.

Kronenwerth et al. "Bioactive Derivatives of Isopropylstilbene from Mutasynthesis and Chemical Synthesis" Oct. 24, 2014, Chembiochem 15(18):2689-2691, DOI:10.1002/cbic.201402447, ISSN 1439-4227, XP055825654.

Krow et al. "Synthesis of Antibiotic Stilbenes Using Organomanganese Arene Complexes" 1992, The J. Organic Chemistry 57(14):4040-4043.

Leraux et al. "Condensation of Aldehydes AlphaBeta Unsaturates on Saturated Cetones" 1968, 14th Ed. Annals of Chemistry and Physics, 21 Pages.

Majima et al. "Cis-trans Isomerization and Oxidation of Radical Cations of Stilbene Derivatives" 1996, The J. Organic Chemistry 61:7793-7800.

Marta et al. "Synthesis of longistylin A, B, C, D and Other New Prenylated Stilbenes" 1980, CA 92:11061(2 Pages).

Ney et al. "Anti-inflammatory Effects of Synthetic Effects of Synthetic Retinoids may be Related to their Immunomodulatory Action" 1987, Dermatologica. 175(1):93-99.

Poldy et al. "Pheromones and Analogs from Neozeleboria Wasps and the Orchids that Seduce them: A Versatile Synthesis of 2,5-Dialkylated 1,3-Cyclohexanediones" Feb. 13, 2008, Tetrahedron Letters, Elsevier, Amsterdam, NL, 49(15):2446-2449, DOI: 10.1016/J.TETLET.2008.02.037, ISSN 0040-4039, XP022523647.

Schamp et al. "New Synthesis of 2-Substituted Resorcinols" Jan. 1, 1973, Tetrahedron, Elsevier Sience Publishers, Amsterdam, NL, 29(23):3857-3859, DOI: 10.1016/0040-4020(73)80207-8, ISSN 0040-4020, XP026636606.

Third Party Observations for Israeli Patent Application No. 274439 submitted on Jul. 27, 2021, 4 pages.

Third Party Observations Submitted on Jul. 27, 2021 in European Patent Application No. 18875722.3, 4 Pages.

Zafiriadis et al. "Raney Nickel Hydrogenation of Cinnamal-Methylisobutyl ketone" Jan. 17, 1949, Weekly Reports of the Sessions of the Academy of Sciences 228:4 Pages, ISSN 0001-4036, (with English Abstract).

Zhang et al. "The Preparation of 3,5-Dihydroxy-4-Isopropylstilbene Nanoemulsion and In Vitro Release" 2011, International Journal of Nanomedicine 6:649-657.

\* cited by examiner

PROCESS FOR PREPARING TAPINAROF

CROSS REFERENCE TO RELATED APPLICATION

The present application is a Continuation of U.S. application Ser. No. 17/174,566, filed Feb. 12, 2021, which is a Continuation of U.S. application Ser. No. 16/849,346, filed Apr. 15, 2020, now U.S. Pat. No. 10,961,175, which is a Continuation of U.S. application Ser. No. 16/189,268, filed Nov. 13, 2018, now U.S. Pat. No. 10,647,649, which claims benefit of and priority to U.S. Provisional No. 62/584,192 entitled "PROCESS," filed Nov. 10, 2017, the contents of which are herein incorporated by reference in their entirety.

SUMMARY OF THE INVENTION

Some embodiments of the present invention provides a processes for the preparation of the compound of Formula (I) or a salt thereof and to novel intermediates used therein

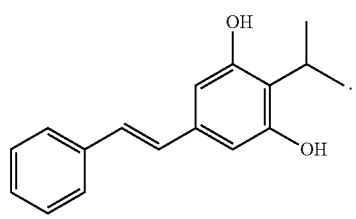
(I)

Some embodiments of the present invention describe a compound of Formula (IIa) or a salt thereof

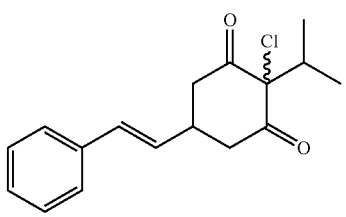
(IIa)

and processes for preparing same.

Some embodiments of the present invention describe a compound of Formula (IVa) or a salt thereof

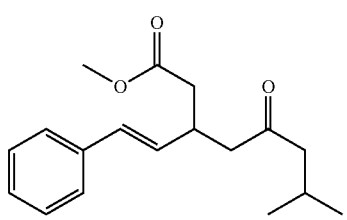
(IVa)

and processes for preparing same.

Some embodiments of the present invention describe a compound of Formula (V) or a salt thereof

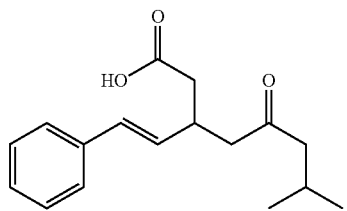
(V)

and processes for preparing same.

Some embodiments of the present invention describe a compound of Formula (VI) or a salt thereof

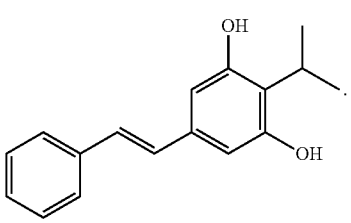
(VI)

and processes for preparing same.

Some embodiments of the present invention describe a pharmaceutical composition which comprises a compound of Formula (I) or a salt or solvate thereof prepared according to the processes of the present invention and a pharmaceutically acceptable excipient.

Figure 1:
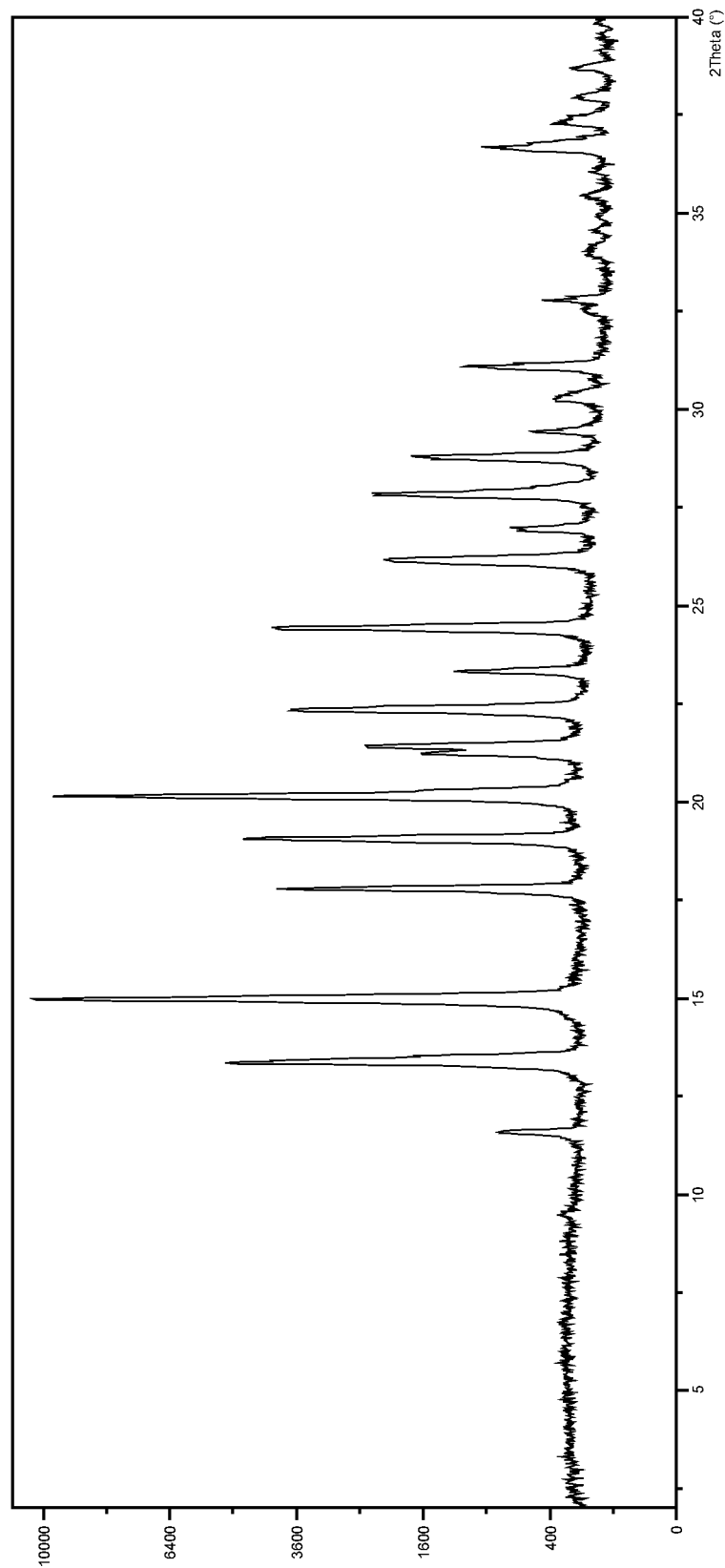
FIG. 1 shows an X-ray powder diffraction (XRPD) pattern of the compound of Formula (I) in crystalline solid state form (Form 1).

DETAILED DESCRIPTION OF THE INVENTION 3,5-Dihydroxy-4-isopropyl-trans-stilbene, also known as (E)-2-isopropyl-5-styrylbenzene-1,3-diol or tapinarof, of Formula (I) is a natural product derived from bacteria

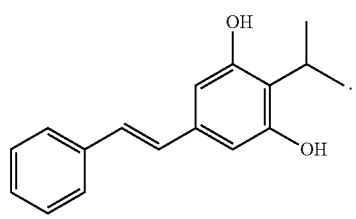
(I)

This compound has several potentially useful biological responses including antibacterial, antioxidant and anti-cancer activity. PCT patent application WO200142231 discloses polyhydroxystilbenes and stilbene oxides as antipsoriatic agents and protein kinase inhibitors.

Several routes to the synthesis of the compound of Formula (I) are known in the art. Chinese patent application CN101648851 describes a route of synthesis via the formation of the (E)-olefin via Horner-Wadsworth-Emmons olefination. Routes are also known which are via the introduction of the isopropyl group onto a substituted resorcinol derivative via Friedel-Crafts alkylation.

An alternative synthetic approach, similar to known biosynthesis route, was described by Kronenwerth et al. (*Eur. J. Org. Chem.* 2014, 8026-8028). In this route, however, there are problems throughout the synthesis with low yields of the intermediates and the final product. There is also a toxicity problem associated with incomplete removal of trace amounts of mercury in isopropylstilbene which makes this route unsuitable for large scale manufacturing of a pharmaceutical product.

Schamp et al. (*Tetrahedron*, 1973, 29, 3857-3859) discloses a synthesis of simple 2-substituted resorcinols such as 2-methyl-, 2-benzyl- and 2-acetylresourcinol from the corresponding 1,3-cyclohexanediones. The reported conditions involve the chlorination of the 1,3-cyclohexanediones followed by elimination of HCl upon heating with a 25% solution of dry hydrogen chloride in dimethylformamide.

There exists a need for an efficient and scalable route for the large scale manufacturing of the compound of Formula (I), in particular a high yielding synthesis with no potential toxicity problems.

The present invention provides a number of embodiments relating to a process which is summarised in Scheme 1 below:

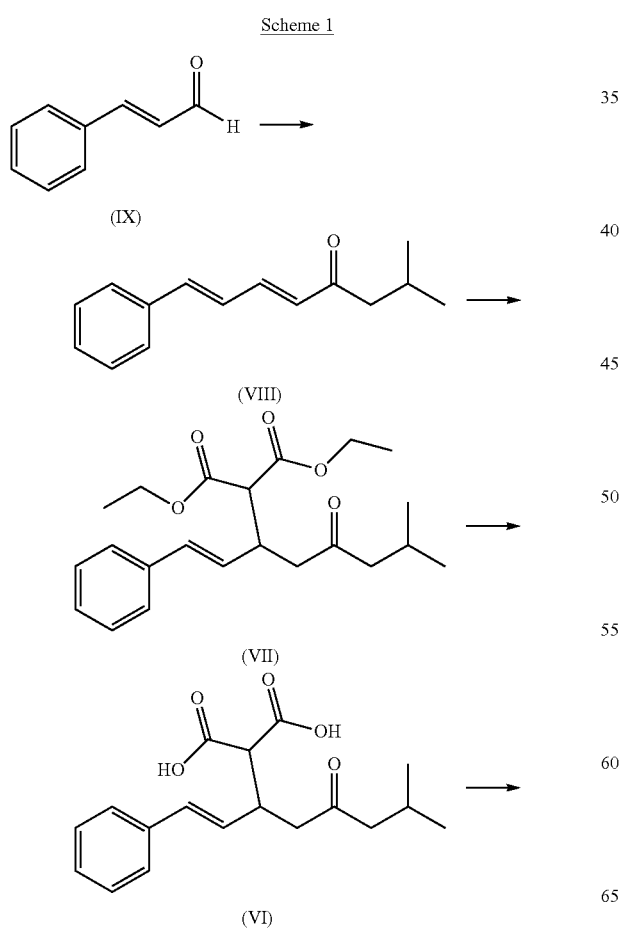
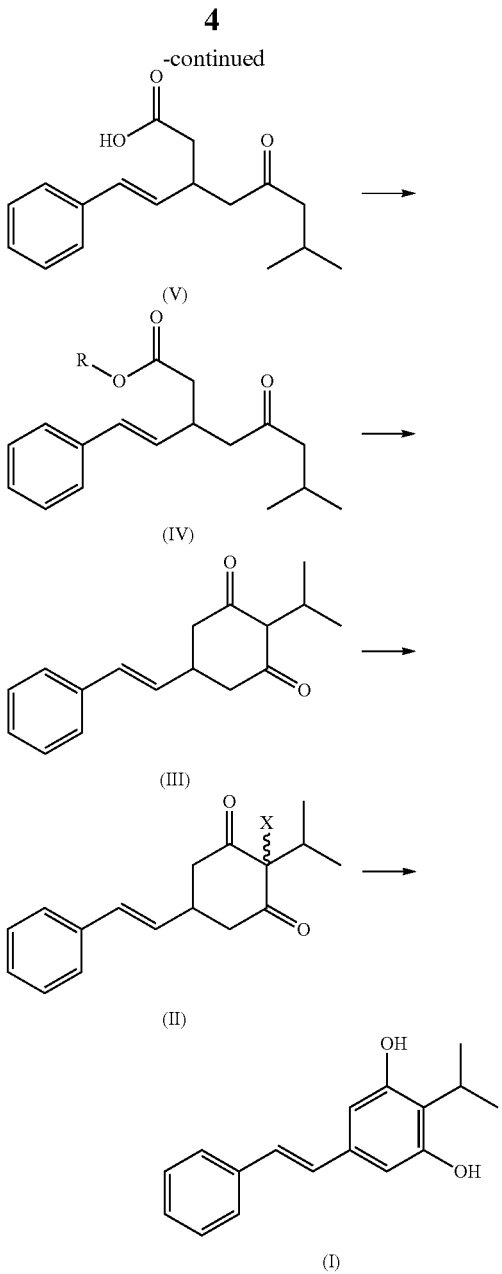

Preparation of the Compound of Formula (I)-Process A

Some embodiments describe a process for the preparation of a compound of Formula (I) or a salt or solvate thereof

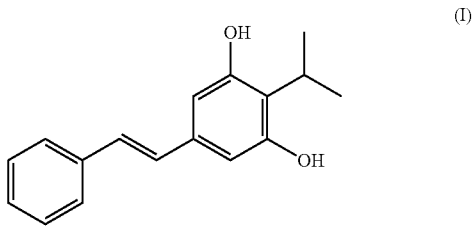 [SMILES: CC(C)c1c(O)cc(/C=C/c2ccccc2)cc1O]

comprising one or more of the process steps (a), (b) and (c) wherein:

(a) comprises reaction of a compound of Formula (III) or a salt thereof

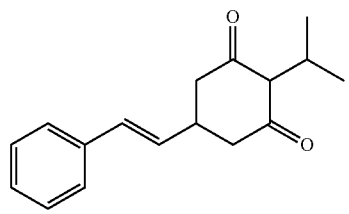
(III)

to form a compound of Formula (II) or a salt thereof

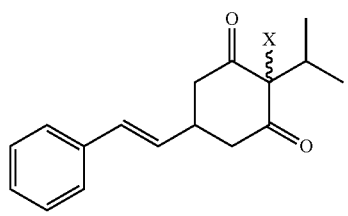
(II)

wherein X is Cl, Br, or I, and thereafter (ii) conversion of the compound of Formula (II) or a salt thereof into the compound of Formula (I) or a salt or solvate thereof;

(b) comprises conversion of a compound of Formula (VI) or a salt thereof

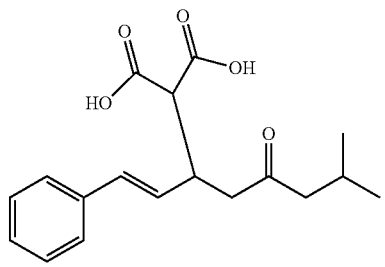
(VI)

into a compound of Formula (III) or a salt thereof

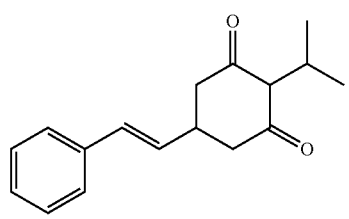
(III)

and thereafter conversion of the compound of Formula (III) or a salt thereof into a compound of Formula (I) or a salt or solvate thereof, and (c) comprises conversion of a compound of Formula (IX) or a salt thereof

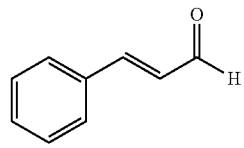
(IX)

into a compound of Formula (VI) or a salt thereof

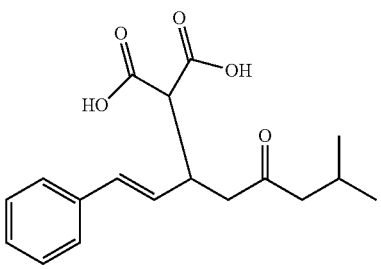
(VI)

and thereafter conversion of the compound of Formula (VI) or a salt thereof into a compound of Formula (I) or a salt or solvate thereof.

Some embodiments describe processes for making compounds of Formula (I) or a salt or solvate thereof comprising at least one of process steps (a) to (c). The processes of the present invention may include one, two or all three of process steps (a), (b) and (c).

The product of each of process steps (a), (b) and (c) may optionally be crystallised.

In some embodiments the compound of Formula (I) prepared by process (a), (b) or (c) is in crystalline solid state form. In one embodiment, there is provided, the compound of Formula (I) in crystalline solid state form (Form 1) which has an X-ray powder diffraction pattern substantially as shown in FIG. 1. In another embodiment there is provided the compound of Formula (I) in crystalline solid state characterised by an X-ray powder diffraction (XRPD) pattern with specific peaks at 15.0, 17.8, 19.1, 20.2, 21.5, 22.4, 23.3, 24.5, 26.2 and 27.9 degrees (all values±0.1° 2θ experimental error). In another embodiment there is provided the compound of Formula (I) in crystalline solid state characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees (all values±0.1° 2θ experimental error).

Process Step (a)

In some embodiments X is Cl.

In some embodiments wherein X is Cl, the reaction is carried out using a chlorination reagent selected from the group consisting of 1,3-dichloro-5,5-dimethylhydantoin (DCDMH), N-chlorosuccinimide (NCS) and trichloroisocyanuric acid (TCCA).

In some embodiments the chlorination reagent is DCDMH.

In some embodiments the conversion of the compound of Formula (II) or a salt thereof to a compound of Formula (I) or a salt thereof is carried out in a suitable solvent and optionally with an additive material.

It was found that such a conversion was achieved in good yields with a number of solvents. In some embodiments the conversion of the compound of Formula (II) or a salt thereof to give a compound of Formula (I) or a salt thereof is carried out in a suitable solvent which is a polar aprotic solvent selected from the group consisting of dimethylformamide (DMF), 1,3-dimethyl-3,4,5,6-tetrahydro-2(1H)-pyrimidinone (DMPU), dimethylacetamide (DMAC) and sulfolane.

Whilst the use of a solvent such as DMF was operationally simple, the use of such in the manufacture of a pharmaceutical product is a matter of potential concern due to its reproductive toxicity. An alternative solvent was therefore sought that would be suitable for use in the large scale manufacture of a pharmaceutical product.

It was found, however, that the conversion of the compound of Formula (II) or a salt thereof, e.g. wherein X is Cl, to a compound of Formula (I) or a salt thereof did not progress well for alternative solvents, including some commonly used solvents. In such circumstances it was found that use of an additive material, such as benzylethylammonium chloride, facilitated this reaction in good yields. This is demonstrated in Table 1 below.

TABLE 1

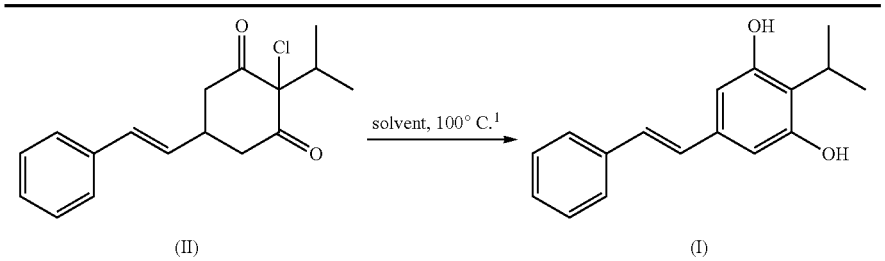

| Solvent | Yield without additive | Yield with additive[2,3] |
|---|---|---|
| Acetonitrile | No product | 96% |
| Toluene | No product | 98% |
| 2-Me-THF | No product | 95% |
| i-PrOAc | <5% | 93% |

[1]Reaction were carried out in sealed tubes which allowed for heating well above the boiling point of the solvent.
[2]Additive = 2 equivalents of benzyltriethylammonium chloride.
[3]Yields based on HPLC assay of crude reaction mixture.

A further investigation was therefore carried out into the use of a range of different additive materials in the conversion of the compound of Formula (II) or a salt thereof, in which X is Cl, to a compound of Formula (I) or a salt or solvate thereof. These results are represented in Table 2 below.

TABLE 2

| Additive | Time | Yield[1] |
|---|---|---|
| BnEt$_3$Cl | 4 hours | 96% |
| Bu$_4$NCl | 4 hours | 93% |
| Et$_4$NCl | 4 hours | 99% |
| Me$_4$NCl | Overnight | 90% |
| cysteine•HCl | Overnight | 8% |
| NH$_4$Cl | Overnight | Trace |
| imidazole•HCl | 5 hours | 20% |
| Et$_3$N•HCl | Overnight | 88% |
| Conc. HCl | 5 hours | 31% |
| NaCl | Overnight | Trace |
| LiCl | Overnight | 20% |

[1]Yields based on HPLC assay of crude reaction mixture.

In some embodiments the conversion of the compound of Formula (II) or a salt thereof to a compound of Formula (I) or a salt thereof is carried out in the presence of an additive reagent which is a quaternary ammonium salt, for example a quaternary ammonium bromide salt or a quaternary ammonium chloride salt. In some embodiments the quaternary ammonium bromide salt is tetrabutylammonium bromide. In some embodiments the quaternary ammonium chloride salt is selected from the group consisting of benzyltriethylammonium chloride, tetrabutylammonium chloride, tetraethylammonium chloride and tetramethylammonium chloride.

In some embodiments the quaternary ammonium chloride salt is tetraethylammonium chloride. In some embodiments the conversion of the compound of Formula (II) or a salt thereof to give a compound of Formula (I) or a salt or a solvate thereof in the presence of an additive reagent is carried out in a solvent selected from the group consisting of acetonitrile, toluene, 2-methyl tetrahydrofuran, isopropyl acetate, acetone and methyl isobutyl ketone. It was found that acetonitrile provided the best combination of solubility and high boiling point. In some embodiments this conversion is carried out in a solvent which is acetonitrile.

Embodiments of the present disclosure describe a compound of Formula (IIa) or a salt thereof

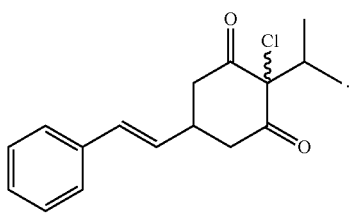

(IIa)

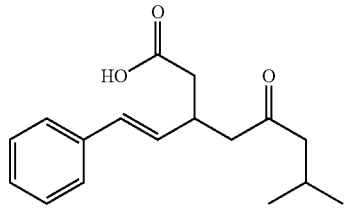

(V)

followed by esterification of the compound of Formula (V) or a salt thereof to form the compound of Formula (IV) or a salt thereof

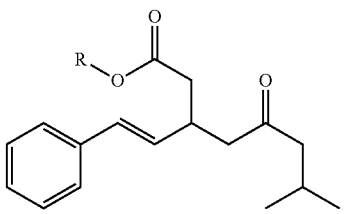

(IV)

wherein R is $C_{1-4}$ alkyl; and thereafter cyclization of the compound of Formula (IV) or a salt thereof to form the compound of Formula (III) or a salt thereof.

In some embodiments conversion of a compound of Formula (VI) or a salt thereof into a compound of Formula (V) or a salt thereof comprises decarboxylation in the presence of a base. In some embodiments the base is selected from imidazole, pyridine, and lutidine (2,6-dimethylpyridine). In a particular embodiments the base is triethylamine.

In some embodiments R is methyl, ethyl, propyl, or butyl. In some embodiments R is t-butyl. In some embodiments R is methyl.

The compound of Formula (I) may be prepared in the form of an acetic acid solvate thereof. Some embodiments of the present disclosure describe a compound of Formula (I) in the form of an acetic acid solvate thereof. It has been found that formation of the acetic acid solvate of the compound of Formula (I) provides impurity and colour purging capabilities to the process of the invention. The acetic acid solvate of the compound of Formula (I) can thereafter be converted into the compound of Formula (I).

Figure 2:
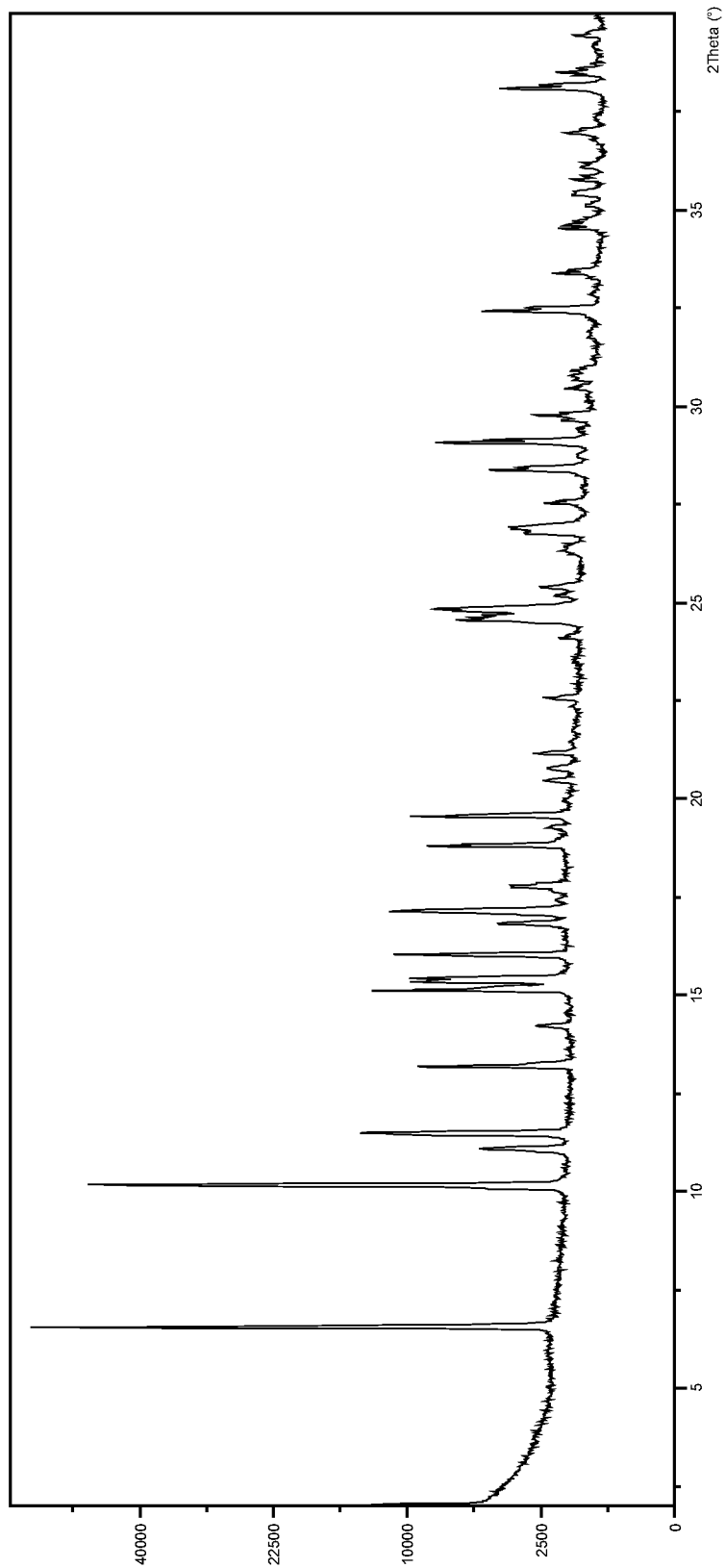
FIG. 2 shows an X-ray powder diffraction (XRPD) pattern of an acetic acid solvate of the compound of Formula (I) in crystalline solid state form.

In some embodiments there is provided an acetic acid solvate of the compound of Formula (I) in crystalline solid state form. In some embodiments, there is provided, an acetic acid solvate of the compound of Formula (I) in crystalline solid state form which has an X-ray powder diffraction pattern substantially as shown in FIG. 2. In another embodiment there is provided an acetic acid solvate of the compound of Formula (I) in crystalline solid state characterised by an X-ray powder diffraction (XRPD) pattern with specific peaks at 6.7, 10.2, 11.1, 15.4, 16.9, 17.2, and 24.8 degrees (all 2θ values, ±0.1° 2θ experimental error). In another embodiment there is provided an acetic acid solvate of the compound of Formula (I) in crystalline solid state characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees (all 2θ values, ±0.1° 2θ experimental error).

In some embodiments the process further comprises a step of recrystallization of the compound of Formula (I) or a salt or solvate thereof. In some embodiments recrystallization is carried out using methanol and water.

Process Step (b)

In some embodiments conversion of a compound of Formula (VI) or a salt thereof into a compound of Formula (III) or a salt thereof comprises a decarboxylation of the compound of Formula (VI) or a salt thereof to form the compound of Formula (V) or a salt thereof In some embodiments esterification of a compound of Formula (V) or a salt thereof to a compound of Formula (IV) or a salt thereof is performed using methanol, for example esterification is performed using methanol and hydrochloric acid.

In some embodiments cyclization of a compound of Formula (IV) or a salt thereof to a compound of Formula (III) or a salt thereof is performed using potassium tert-butoxide.

In some embodiments the compound of Formula (III) or a salt thereof is acidified and isolated by precipitation with methylcyclohexane.

In some embodiments the conversion of a compound of Formula (VI) or a salt thereof into a compound of Formula (III) or a salt thereof is telescoped such that the compounds of Formula (V) or a salt thereof and Formula (IV) or a salt thereof are not isolated.

Some embodiments describe a compound of Formula (IVa) or a salt thereof

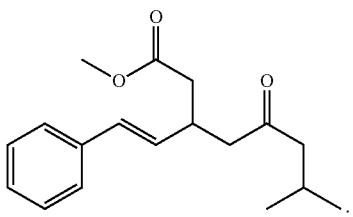
(IVa)

The compound of Formula (IVa), namely (E)-methyl 7-methyl-5-oxo-3-styryloctanoate, is characterized by the following data.

$^1$H NMR (500 MHz, DMSO) δ 7.33 (m, 2H), 7.29 (m, 2H), 7.20 (m, 1H), 6.37 (d, 1H, J=16.0 Hz), 6.15 (dd, 1H, J=8.1 Hz, J=16.0 Hz), 3.56 (s, 3H), 3.09 (m, 1H), 2.60 (m, 2H), 2.50 (dd, 1H, 6.1 Hz, J=15.4 Hz), 2.42 (dd, 1H, J=8.1 Hz, J=15.4 Hz), 2.29 (d, 2H, 7.0 Hz), 2.00 (m, 1H), 0.82 (s, 6H, 6.7 Hz).

$^{13}$C NMR (125 MHz, DMSO) δ 208.7 (C), 171.8 (C), 136.8 (C), 131.9 (CH), 129.5 (CH), 128.5 (CH), 127.2 (CH), 125.9 (CH), 51.4 (CH$_2$), 51.2 (CH$_3$), 46.7 (CH$_2$), 38.5 (CH$_2$), 34.4 (CH), 23.8 (CH), 22.29 (CH$_3$), 22.26 (CH$_3$).

HRMS-APCI (m/z) [M+H]$^+$ calculated for C$_{18}$H$_{25}$O$_3$, 289.1798; found, 289.1719.

In a some embodiments there is provided a compound of Formula (V) or a salt thereof

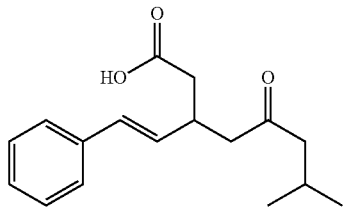
(V)

The compound of Formula (V), namely (E)-7-methyl-5-oxo-3-styryloctanoic acid, is characterized by the following data.

$^1$H NMR (700 MHz, DMSO) δ 12.13 (s, 1H), 7.33 (m, 2H), 7.29 (m, 2H), 7.20 (m, 1H), 6.37 (d, 1H, J=16 Hz), 6.17 (dd, 1H, J=8.0 Hz, J=16.0 Hz), 3.07 (m, 1H), 2.60 (m, 2H), 2.46 (dd, 1H, J=6.2 Hz, J=15.5 Hz), 2.33 (dd, 1H, J=8.0, J=15.5 Hz), 2.30 (d, 2H, J=7.1 Hz), 2.0 (m, 1H), 0.82 (d, 6H, J=6.6 Hz).

$^{13}$C NMR (176 MH, DMSO) δ 208.8 (C), 172.9 (C), 136.9 (C), 132.2 (CH), 129.3 (CH), 128.5 (CH), 127.1 (CH), 125.9 (CH), 51.4 (CH$_2$), 46.8 (CH$_2$), 38.9 (CH$_2$), 34.4 (CH), 23.8 (CH), 22.3 (CH$_3$), 22.3 (CH$_3$).

HRMS-APCI (m/z) [M+H]$^+$ calcd for C$_{17}$H$_{23}$O$_3$, 275.1642; found, 275.1635.

In some embodiments there is provided a compound of Formula (VI) or a salt thereof.

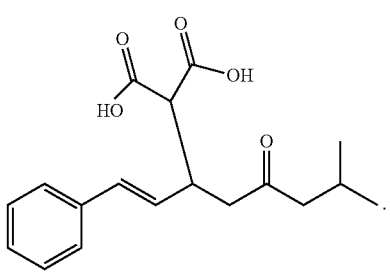
(VI)

The compound of Formula (III) or a salt thereof may be converted into a compound of Formula (I) or a salt or solvate thereof by methods described herein (e.g. process step (a)) or by methods known to the person skilled in the art (e.g. by methods described in Kronenwerth, M. et al.). In some embodiments the compound of Formula (III) or a salt thereof may be converted into a compound of Formula (I) or a salt or solvate thereof by process step (a).

Process Step (c)

In some embodiments conversion of a compound of Formula (IX) or a salt thereof into a compound of Formula (VI) or a salt thereof comprises the condensation of the compound of Formula (IX) or a salt thereof with methyl isobutyl ketone to form the compound of Formula (VIII) or a salt thereof

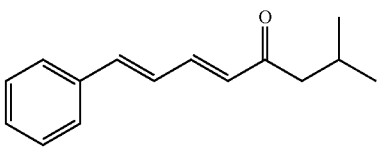
(VIII)

followed by addition of a malonic ester (R$_1$O(O)C—CH$_2$—C(O)OR$_2$) to form a compound of Formula (VII) or a salt thereof

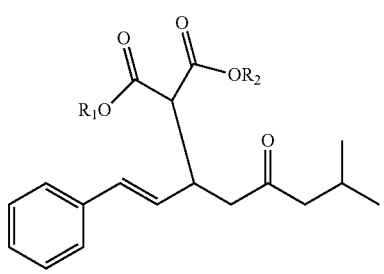
(VII)

wherein R$_1$ and R$_2$ are independently C$_{1-4}$ alkyl;
and thereafter hydrolysation of the compound of Formula (VII) or a salt thereof to form the compound of Formula (VI) or a salt thereof.

In some embodiments condensation of a compound of Formula (IX) or a salt thereof into a compound of Formula (VIII) or a salt thereof is performed using lithium, potassium or sodium hydroxide, for example the condensation is performed using potassium or sodium hydroxide in methanol.

In some embodiments the conversion of a compound of Formula (VIII) or a salt thereof into a compound of Formula (VII) or a salt thereof comprises the addition of a malonic ester which is di-tert-butyl malonate or diethyl malonate.

In some embodiments the conversion of a compound of Formula (IX) or a salt thereof into a compound of Formula (VI) or a salt thereof is telescoped such that the compounds of Formula (VII) and Formula (VIII) or salts thereof are not isolated.

In some embodiments there is provided a compound of Formula (VIIa) or a salt thereof.

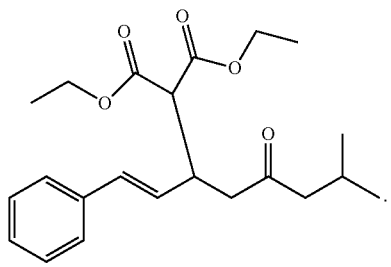

(VIIa)

The compound of Formula (VIIa), namely (E)-diethyl 2-(7-methyl-5-oxo-1-phenyloct-1-en-3-yl)malonate, is characterized by the following data.

$^1$H NMR (700 MHz, DMSO) δ 7.30 (m, 2H), 7.30 (m, SH0, 7.21 (m, 1H), 6.39 (d, 1H) J=15.8 Hz), 6.14 (dd, 1H, J=15.99 Hz, J=8.9 Hz), 4.12 (q, 2H, J=7.13 Hz), 4.06 (m, 2H), 3.68 (d, 1H, J=8.1 Hz), 3.33 (m, 1H), 2.73 (dd, 1H, J=16.9 Hz, J=9.0 Hz), 2.63 (m, 1H), 2.28 (d, 2H, 6.9 Hz), 1.98 (m, 1H, 6.7 Hz), 1.16 (t, 3H, J=7.1 Hz), 1.10 (t, 3H, J=7.0 Hz), 0.81 (d, 3H, J=6.6 Hz), 0.80 (d, 3H, J=6.7 Hz).

$^{13}$C NMR (176 MHz, DMSO) δ 208.1 (C), 167.7 (C), 167.6 (C), 136.6 (C), 131.4 (CH), 128.9 (CH), 127.4 (CH), 125.9 (CH), 61.0 (CH2), 60.8 (CH2), 55.0 (CH), 51.3 (CH2), 44.8 (CH2), 37.7 (CH), 23.8 (CH), 22.3 (CH3), 22.2 (CH3), 13.9 (CH3), 13.9 (CH3).

HRMS-APCI (m/z) [M+H]$^+$ calcd for $C_{22}H_{31}O_5$, 375.2166; found, 375.2158.

The compound of Formula (VI) or a salt thereof may be converted into a compound of Formula (I) or a salt or solvate thereof by methods described herein (e.g. process steps (a) and (b)) or by methods known to the person skilled in the art (e.g. by methods described in Kronenwerth, M. et al.). In some embodiments the compound of Formula (VI) or a salt thereof may be converted into a compound of Formula (I) or a salt or solvate thereof by process steps (a) and (b).

Preparation of the Compound of Formula (I)-Process B

Some embodiments herein describe a process for preparing a compound of Formula (I) or salt or solvate thereof

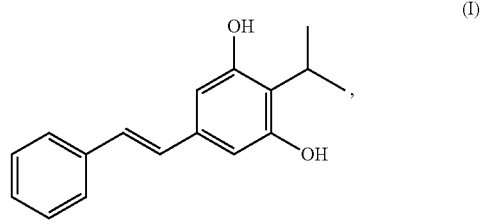 [SMILES: CC(C)c1c(O)cc(/C=C/c2ccccc2)cc1O]

(I)

comprising aromatizing a compound of Formula (II) or salt thereof

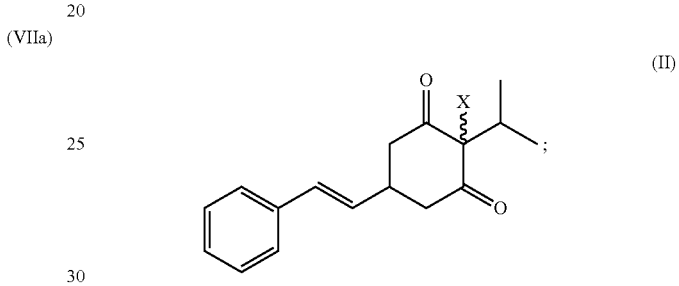

(II)

wherein X is Cl, Br, or I; to obtain the compound of Formula (I). In some embodiments the process further comprises purifying the compound of Formula (I) or a salt or solvate thereof. In some embodiments the purifying comprises crystallization of the compound of Formula (I) or a salt or solvate thereof. In some embodiments the compound of Formula (I) is a crystal form described in any embodiment described herein. In some embodiments the compound of Formula (I) is crystal form 1. In some embodiments the compound of Formula (I) is an anhydrous crystal. In some embodiments the compound of Formula (I) has an X-ray powder diffraction pattern substantially as shown in FIG. 1. In some embodiments the compound of Formula (I) is in a crystalline solid state characterised by an X-ray powder diffraction (XRPD) pattern with specific peaks at 15.0, 17.8, 19.1, 20.2, 21.5, 22.4, 23.3, 24.5, 26.2 and 27.9 degrees (all values±0.1° 2θ experimental error). In some embodiments the compound of Formula (I) is in a crystalline solid state characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees (all values±0.1° 2θ experimental error). In some embodiments the compound of Formula (I) is an acetic acid solvate in crystalline solid state form. In some embodiments, the compound of Formula (I) is an acetic acid solvate in crystalline solid state form which has an X-ray powder diffraction pattern substantially as shown in FIG. 2. In another embodiment the compound of Formula (I) is an acetic acid solvate in crystalline solid state characterised by an X-ray powder diffraction (XRPD) pattern with specific peaks at 6.7, 10.2, 11.1, 15.4, 16.9, 17.2, and 24.8 degrees (all 2θ values, ±0.1° 2θ experimental error). In another embodiment the compound of Formula (I) is an acetic acid solvate in crystalline solid state characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees (all 2θ values, ±0.1° 2θ experimental error). In some embodiments X is Cl. In some embodiments the aromatizing is carried out in a suitable solvent and optionally with an additive reagent. In some embodiments the aromatizing is carried out in a suitable solvent which is a polar aprotic solvent selected from the group consisting of dimethylformamide (DMF), 1,3-dimethyl-3,4,5,6-tetrahydro-2(1H)-pyrimidinone. In some embodiments the aromatizing is carried out in the presence of an additive reagent in a solvent selected from the group consisting of acetonitrile, toluene, 2-methyl tetrahydrofuran, isopropyl acetate, acetone and methyl isobutyl ketone. In some embodiments the aromatizing is carried out in acetonitrile in the presence of an additive reagent. In some embodiments the additive reagent is a quaternary ammonium salt. In some embodiments the quaternary ammonium salt is selected from the group consisting of tetrabutylammonium bromide, benzyltriethylammonium chloride, tetrabutylammonium chloride, tetraethylammonium chloride and tetramethylammonium chloride. In some embodiments the quaternary ammonium salt is tetraethylammonium chloride. In some embodiments the aromatizing is carried out in acetonitrile with tetraetylammonium chloride.

In some embodiments the process further comprises halogenating a compound of Formula (III) or salt thereof

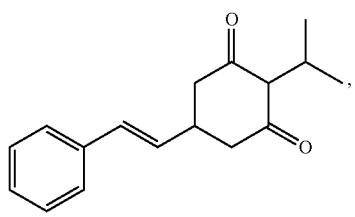

(III)

with a halogenating agent to obtain the compound of Formula (II) or a salt thereof. In some embodiments the halogenating agent is selected from 1,3-dichloro-5,5-dimethylhydantoin (DCDMH); N-chlorosuccinimide (NCS); and trichloroisocyanuric acid (TCCA). In some embodiments the halogenating agent is DCDMH and the compound of Formula (II) or a salt thereof is a compound of Formula (IIa) or a salt thereof:

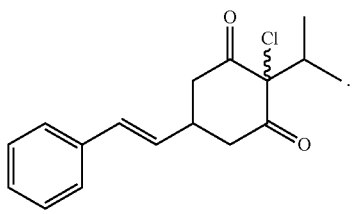

(IIa)

In some embodiments the halogenating is carried out in methanol. In some embodiments the halogenation agent is DCDMH and the halogenation is carried out in methanol.

In some embodiments the process further comprises cyclizing a compound of Formula (IV) or salt thereof

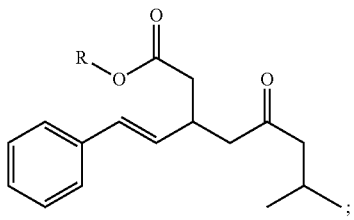

(IV)

wherein R is $C_{1-4}$ alkyl, to obtain the compound of Formula (III) or a salt thereof. In some embodiments R is selected from the group consisting of methyl, ethyl, propyl, or butyl. In some embodiments R is t-butyl. In some embodiments R is methyl. In some embodiments the cyclization comprises contacting the compound of Formula (IV) or a salt thereof, with a base. In some embodiments the cyclization is performed using potassium tert-butoxide. In some embodiments the cyclization is carried out in 2-methyltetrahydrofuran. In some embodiments the cyclization comprises treating a compound of Formula (IV) or a salt thereof, for example a compound of (IVa) or a salt thereof, with potassium tert-butoxide in 2-methyltetrahydrofuran. In some embodiments the compound of Formula (III) or a salt thereof is further acidified and isolated by precipitation with methylcyclohexane.

In some embodiments the process further comprises esterifying a compound of Formula (V) or salt thereof

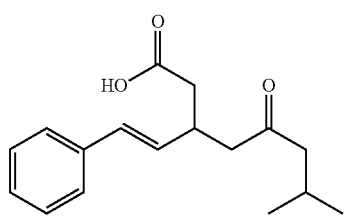

(V)

to obtain the compound of Formula (IV) or a salt thereof. In some embodiments the esterifying is carried out using methanol and hydrochloric acid to obtain compound (IV). In some embodiments the esterifying comprises treating the compound of Formula (V) or a salt thereof with aqueous hydrochloric acid in methanol.

In some embodiments the process further comprising decarboxylating a compound of Formula (VI) or a salt thereof

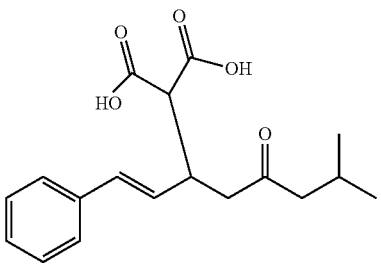

(VI)

to obtain the compound of Formula (V) or a salt thereof. In some embodiments the decarboxylating comprises the presence of a base. In some embodiments the base is selected from imidazole, pyridine, and lutidine (2,6-dimethylpyridine). In some embodiments the base is trimethylamine. In some embodiments the decarboxylating comprises heating the compound of Formula (VI) or a salt thereof in the presence of trimethylamine.

In some embodiments the process further comprises hydrolyzing a compound of Formula (VII) or a salt thereof

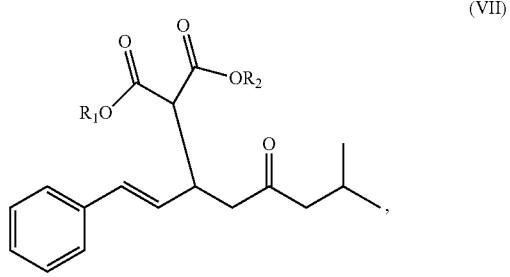

(VII)

wherein each $R_1$ and $R_2$ is independently $C_{1-4}$ alkyl; to obtain the compound of Formula (VI) or a salt thereof. In some embodiments each of $R_1$ and $R_2$ is ethyl (VIIa). In some embodiments the hydrolyzing comprises treating the compound of Formula (VII) or a salt thereof, with sodium hydroxide. In some embodiments the hydrolyzing comprises treating the compound of Formula (VII) or a salt thereof with sodium hydroxide in ethanol. In some embodiments the process comprises hydrolyzing a compound of Formula (VIIa) or a salt thereof comprising treating the compound of Formula (VIIa) or a salt thereof with sodium hydroxide in ethanol.

In some embodiments the process further comprises adding a dialkyl malonic ester ($R_1O(O)C—CH_2—C(O)OR_2$ wherein each $R_1$ and $R_2$ is independently $C_{1-4}$ alkyl), to a compound of Formula (VIII) or a salt thereof

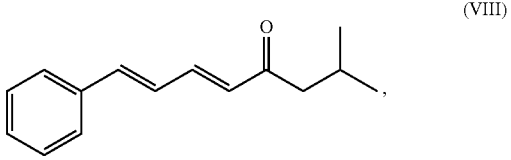 [SMILES: CC(C)CC(=O)/C=C/C=C/c1ccccc1]

(VIII)

to obtain the compound of Formula (VII) or a salt thereof. In some embodiments the dialkyl malonic ester is di-tert-butylmalonate or diethyl malonate. In some embodiments, the adding comprises contacting the dialkyl malonic ester with the compound of Formula (VIII) or a salt thereof in the presence of lithium bromide/triethylamine.

In some embodiments, the process further comprises condensing trans-cinnamaldehyde (compound of Formula (IX)) or a salt thereof

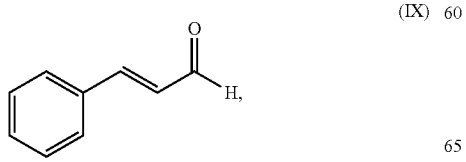

(IX)

with methyl isobutyl ketone to form the compound of Formula (VIII) or a salt thereof. In some embodiments the condensing comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing comprises treating the methyl isobutyl ketone with the trans-cinnamaldehyde or a salt thereof in the presence of sodium hydroxide in methanol.

Preparation of the Compound of Formula (I)-Process C

In some embodiments described herein is a process for preparing a compound of Formula (I) or a salt or solvate thereof

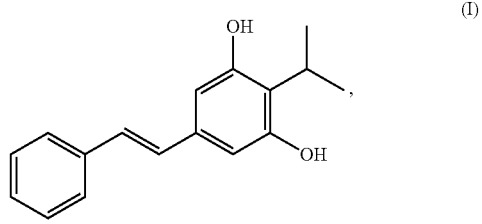 [SMILES: CC(C)c1c(O)cc(/C=C/c2ccccc2)cc1O]

(I)

comprising:

a) decarboxylating a compound of Formula (VI) or a salt thereof

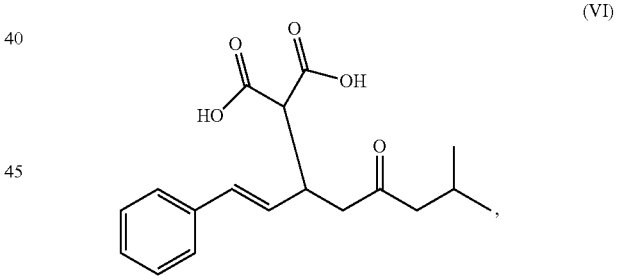

(VI)

to form a compound of Formula (V) or a salt thereof

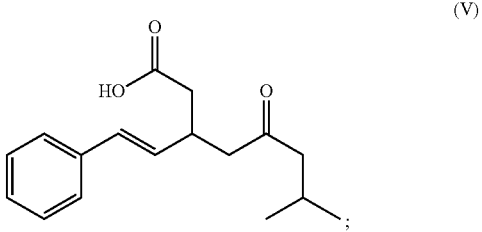 [SMILES: CC(C)CC(=O)CC(/C=C/c1ccccc1)CC(=O)O]

(V)

b) esterifying the compound of Formula (V) or a salt thereof to form a compound of Formula (IV) or a salt thereof

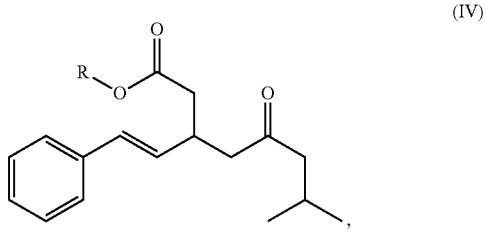

(IV)

wherein R is $C_{1-4}$ alkyl;

c) cyclizing the compound of Formula (IV) or a salt thereof to form a compound of Formula (III) or a salt thereof,

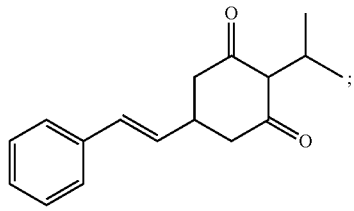

(III)

d) halogenating the compound of Formula (III) or a salt thereof to form a compound of Formula (II) or a salt thereof,

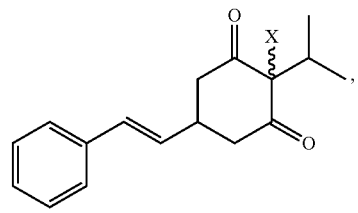

(II)

wherein X is selected from Br, Cl and I; and e) aromatizing the compound of Formula (II) or a salt thereof to form the compound of Formula (I) or a salt or solvate thereof.

In some embodiments the process further comprises isolating the compound of Formula (III) or a salt thereof in step c). In some embodiments the process comprises isolating the compound of Formula (II) or a salt thereof in step d). In some embodiments the process further comprises purifying the compound of Formula (I) or a salt or solvate thereof obtained from step e). In some embodiments the purifying comprises crystallization of the compound of Formula (I) or a salt or solvate thereof. In some embodiments the compound of Formula (I) is a crystal form described in any embodiment described herein. In some embodiments the compound of Formula (I) is crystal form 1. In some embodiments the compound of Formula (I) is an anhydrous crystal. In some embodiments the compound of Formula (I) has an X-ray powder diffraction pattern substantially as shown in FIG. 1. In some embodiments the compound of Formula (I) is in a crystalline solid state characterised by an X-ray powder diffraction (XRPD) pattern with specific peaks at 15.0, 17.8, 19.1, 20.2, 21.5, 22.4, 23.3, 24.5, 26.2 and 27.9 degrees (all values±0.1° 2θ experimental error). In some embodiments the compound of Formula (I) is in a crystalline solid state characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees (all values±0.1° 2θ experimental error). In some embodiments the compound of Formula (I) is an acetic acid solvate in crystalline solid state form. In some embodiments, the compound of Formula (I) is an acetic acid solvate in crystalline solid state form which has an X-ray powder diffraction pattern substantially as shown in FIG. 2. In another embodiment the compound of Formula (I) is an acetic acid solvate in crystalline solid state characterised by an X-ray powder diffraction (XRPD) pattern with specific peaks at 6.7, 10.2, 11.1, 15.4, 16.9, 17.2, and 24.8 degrees (all 2θ values, ±0.1° 2θ experimental error). In another embodiment the compound of Formula (I) is an acetic acid solvate in crystalline solid state characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees (all 2θ values, ±0.1° 2θ experimental error).

In some embodiments the decarboxylating of a compound of Formula (VI) or a salt thereof in step a) comprises the presence of a base. In some embodiments the base is selected from imidazole, pyridine, and lutidine (2,6-dimethylpyridine). In some embodiments the base is trimethylamine. In some embodiments the decarboxylating comprises heating the compound of Formula (VI) or a salt thereof in the presence of trimethylamine.

In some embodiments R of the compound of Formula (IV) or a salt thereof in step b) is selected from the group consisting of methyl, ethyl, propyl, or butyl. In some embodiments R of the compound of Formula (IV) or a salt thereof in step b) is t-butyl. In some embodiments R of the compound of Formula (IV) or a salt thereof in step b) is methyl. In some embodiments the esterifying of the compound of Formula (V) or a salt thereof in step b) is carried out using methanol and hydrochloric acid to obtain compound (IV) or a salt or solvate thereof. In some embodiments the esterifying comprises treating the compound of Formula (V) or a salt thereof with aqueous hydrochloric acid in methanol.

In some embodiments the cyclization in step c) comprises contacting the compound of Formula (IV) or salt thereof with a base. In some embodiments the cyclization is performed using potassium tert-butoxide. In some embodiments the cyclization is carried out in 2-methyltetrahydrofuran. In some embodiments the cyclization comprises treating a compound of Formula (IV) or a salt thereof, for example a compound of (IVa) or a salt thereof, with potassium tert-butoxide in 2-methyltetrahydrofuran. In some embodiments the compound of Formula (III) or a salt thereof is further acidified and isolated by precipitation with methylcyclohexane.

In some embodiments X of the compound of Formula (II) or a salt thereof in step d) is Cl, Br, or I. In some embodiments X of the compound of Formula (II) or a salt thereof in step d) is Cl. In some embodiments the halogenating comprises treating the compound of Formula (III) or a salt thereof with a halogenating agent. In some embodiments the halogenating agent is selected from 1,3-dichloro-5,5-dimethylhydantoin (DCDMH); N-chlorosuccinimide (NCS); and trichloroisocyanuric acid (TCCA). In some embodiments the halogenating agent is DCDMH and the compound of Formula (II) or a salt thereof is a compound of Formula (IIa) or a salt thereof.

In some embodiments the aromatizing in step e) is carried out in a suitable solvent and optionally with an additive reagent. In some embodiments the aromatizing in step e) is carried out in a suitable solvent which is a polar aprotic solvent selected from the group consisting of dimethylformamide (DMF), 1,3-dimethyl-3,4,5,6-tetrahydro-2(1H)-pyrimidinone. In some embodiments the aromatizing in step e) is carried out in the presence of an additive reagent in a solvent selected from the group consisting of acetonitrile, toluene, 2-methyl tetrahydrofuran, isopropyl acetate, acetone and methyl isobutyl ketone. In some embodiments the aromatizing is carried out in acetonitrile in the presence of an additive reagent. In some embodiments the additive reagent is a quaternary ammonium salt. In some embodiments the quaternary ammonium salt is selected from the group consisting of tetrabutylammonium bromide, benzyltriethylammonium chloride, tetrabutylammonium chloride, tetraethylammonium chloride and tetramethylammonium chloride. In some embodiments the quaternary ammonium salt is tetraethylammonium chloride. In some embodiments the aromatizing is carried out in acetonitrile with tetraetylammonium chloride.

In some embodiments R of step b) is methyl and X of step d) is chloro.

In some embodiments the compound of Formula (VI) or a salt thereof in step a) is prepared by a process comprising:
i. condensing trans-cinnamaldehyde or a salt thereof with methyl isobutyl ketone to form a compound of Formula (VIII) or a salt thereof

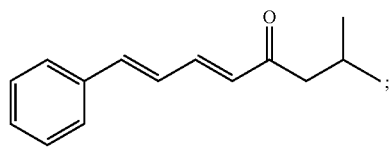
(VIII)

ii. adding a dialkyl malonic ester of the Formula $R_1O(O)C—CH_2—C(O)OR_2$, wherein each of $R_1$ and $R_2$ is independently $C_{1-4}$ alkyl, to the compound of Formula (VIII) or a salt thereof to form a compound of Formula (VII) or a salt thereof

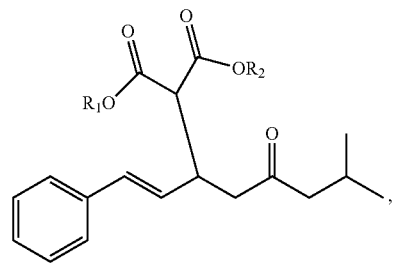
(VII)

wherein each $R_1$ and $R_2$ are as defined for the dialkyl malonic ester;
iii. hydrolyzing the compound of Formula (VII) or a salt thereof, to form the compound of Formula (VI) or a salt thereof.

In some embodiments the condensing in step i. comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step i. comprises treating the methyl isobutyl ketone with the trans-cinnamaldehyde or a salt thereof in the presence of sodium hydroxide in methanol.

In some embodiments each of $R^1$ and $R^2$ in step ii. is ethyl. In some embodiments the dialkyl malonic ester in step ii. is di-tert-butylmalonate or diethyl malonate. In some embodiments, the adding in step ii. comprises contacting the malonic ester with the compound of Formula (VIII) or a salt thereof in the presence of lithium bromide/triethylamine.

Preparation of the Compound of Formula (I)-Process D

Some embodiments herein describe a process for preparing the compound of Formula (I) or a salt or solvate thereof

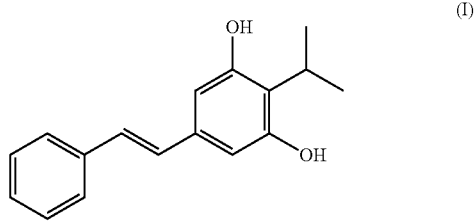 [SMILES: CC(C)c1c(O)cc(/C=C/c2ccccc2)cc1O]
(I)

comprising:
a) heating a compound of Formula (VI)

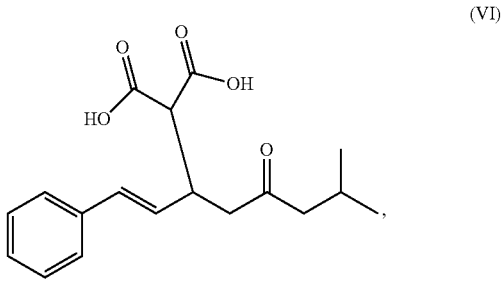 [SMILES: CC(C)CC(=O)CC(/C=C/c1ccccc1)CC(C(=O)O)C(=O)O]
(VI)

with catalytic triethylamine to form a compound of Formula (V)

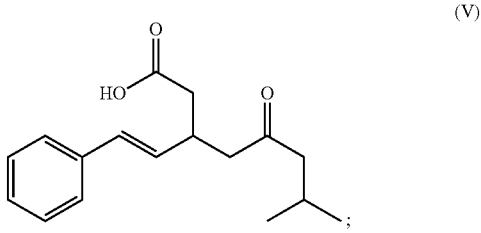 [SMILES: CC(C)CC(=O)CC(/C=C/c1ccccc1)CC(=O)O]
(V)

b) heating the compound of Formula (V) with methanol and aqueous hydrochloric acid to form a compound of Formula (IVa)

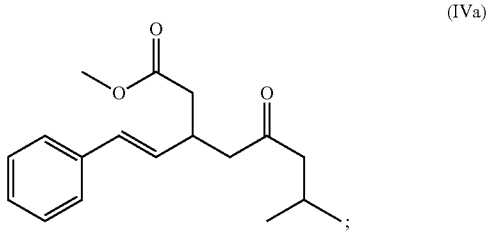 [SMILES: COC(=O)CC(/C=C/c1ccccc1)CC(=O)CC(C)C]

(IVa)

c) treating a cooled solution of the compound of Formula (IVa) with potassium tert-butoxide to form a compound of Formula (III)

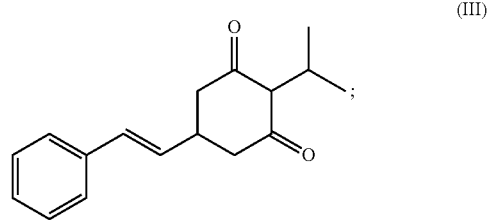 [SMILES: CC(C)C1C(=O)CC(/C=C/c2ccccc2)CC1=O]

(III)

d) heating the compound of Formula (III) with 1,3-dichloro-5,5-dimethylhydantoin to form a compound of Formula (IIa)

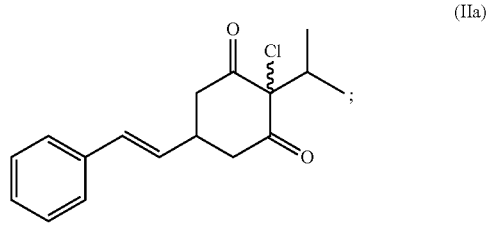 [SMILES: CC(C)C1(Cl)C(=O)CC(/C=C/c2ccccc2)CC1=O]

(IIa)

and e) heating the compound of Formula (IIa) with tetraethylammonium chloride to form the compound of Formula (I) a salt or solvate thereof.

In some embodiments, the process further comprises purifying the compound of Formula (I) from step e) by crystallization. In some embodiments the process further comprises after step c), step ci) isolating the compound of Formula (III). In some embodiments the process further comprises after step d), step di) isolating the compound of Formula (IIa). In some embodiments the process further comprises purifying the compound of Formula (I) obtained from step e). In some embodiments the purifying comprises crystallization of Formula (I). In some embodiments the compound of Formula (I) is a crystal form described in any embodiment described herein. In some embodiments the compound of Formula (I) is crystal form 1. In some embodiments the compound of Formula (I) is an anhydrous crystal. In some embodiments the compound of Formula (I) has an X-ray powder diffraction pattern substantially as shown in FIG. 1. In some embodiments the compound of Formula (I) is in a crystalline solid state characterised by an X-ray powder diffraction (XRPD) pattern with specific peaks at 15.0, 17.8, 19.1, 20.2, 21.5, 22.4, 23.3, 24.5, 26.2 and 27.9 degrees (all values±0.1° 2θ experimental error). In some embodiments the compound of Formula (I) is in a crystalline solid state characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees (all values±0.1° 2θ experimental error). In some embodiments the compound of Formula (I) is an acetic acid solvate in crystalline solid state form. In some embodiments, the compound of Formula (I) is an acetic acid solvate in crystalline solid state form which has an X-ray powder diffraction pattern substantially as shown in FIG. 2.

In another embodiment the compound of Formula (I) is an acetic acid solvate in crystalline solid state characterised by an X-ray powder diffraction (XRPD) pattern with specific peaks at 6.7, 10.2, 11.1, 15.4, 16.9, 17.2, and 24.8 degrees (all 2θ values, ±0.1° 2θ experimental error). In another embodiment the compound of Formula (I) is an acetic acid solvate in crystalline solid state characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees (all 2θ values, ±0.1° 2θ experimental error).

In some embodiments, the compound of Formula (VI) in step a) is prepared by a process comprising:

i. treating methyl isobutyl ketone with trans-cinnamaldehyde in the presence of methanolic sodium hydroxide to form a compound of Formula (VIII)

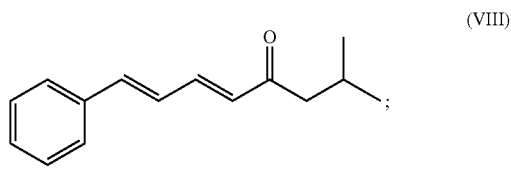 [SMILES: CC(C)CC(=O)/C=C/C=C/c1ccccc1]

(VIII)

ii. treating the compound of Formula (VIII) with diethyl malonate in the presence of lithium bromide and triethylamine to form a compound of Formula (VIIa)

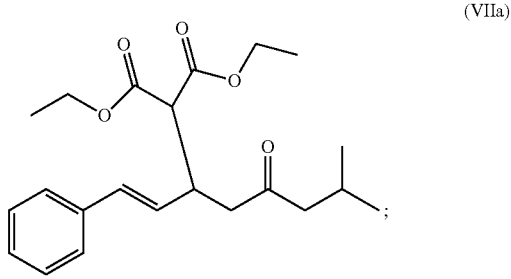 [SMILES: CCOC(=O)C(CC(/C=C/c1ccccc1)CC(=O)CC(C)C)C(=O)OCC]

(VIIa)

iii. hydrolyzing the compound of Formula (VIIa) with sodium hydroxide and ethanol to obtain the compound of Formula (VI).

Preparation of the Compound of Formula (I)-Process E

Some embodiments describe a process for a particular embodiment of the present invention is shown in Scheme 2 below and as described in detail in the Examples.

Scheme 2
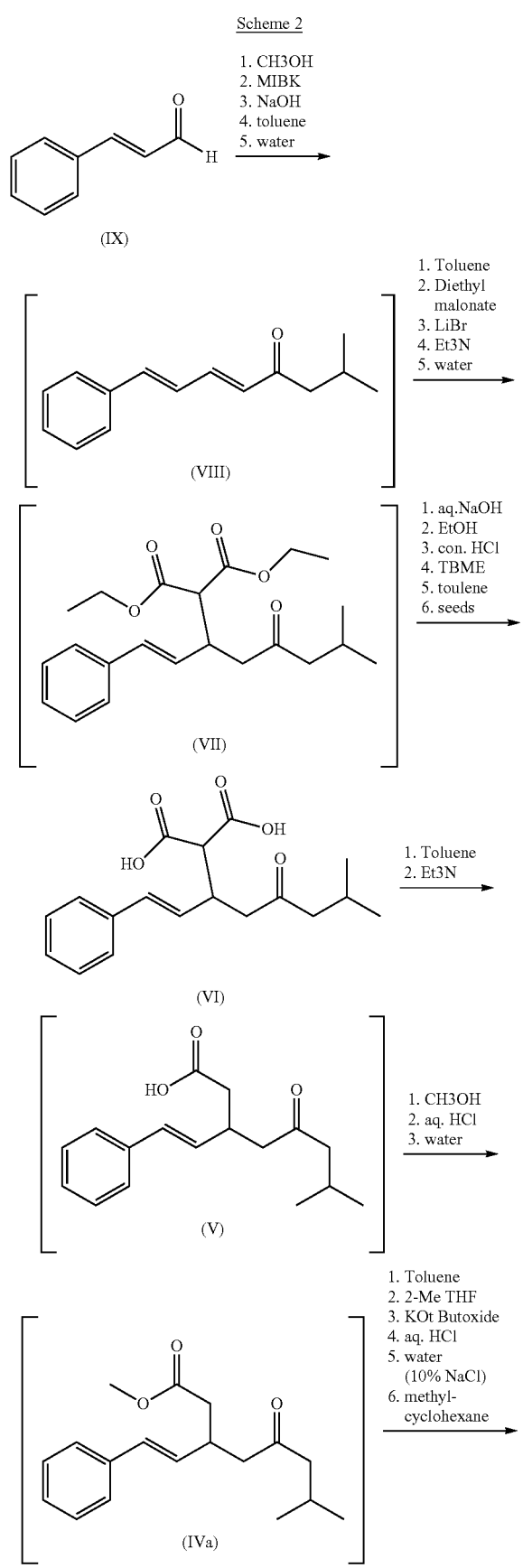
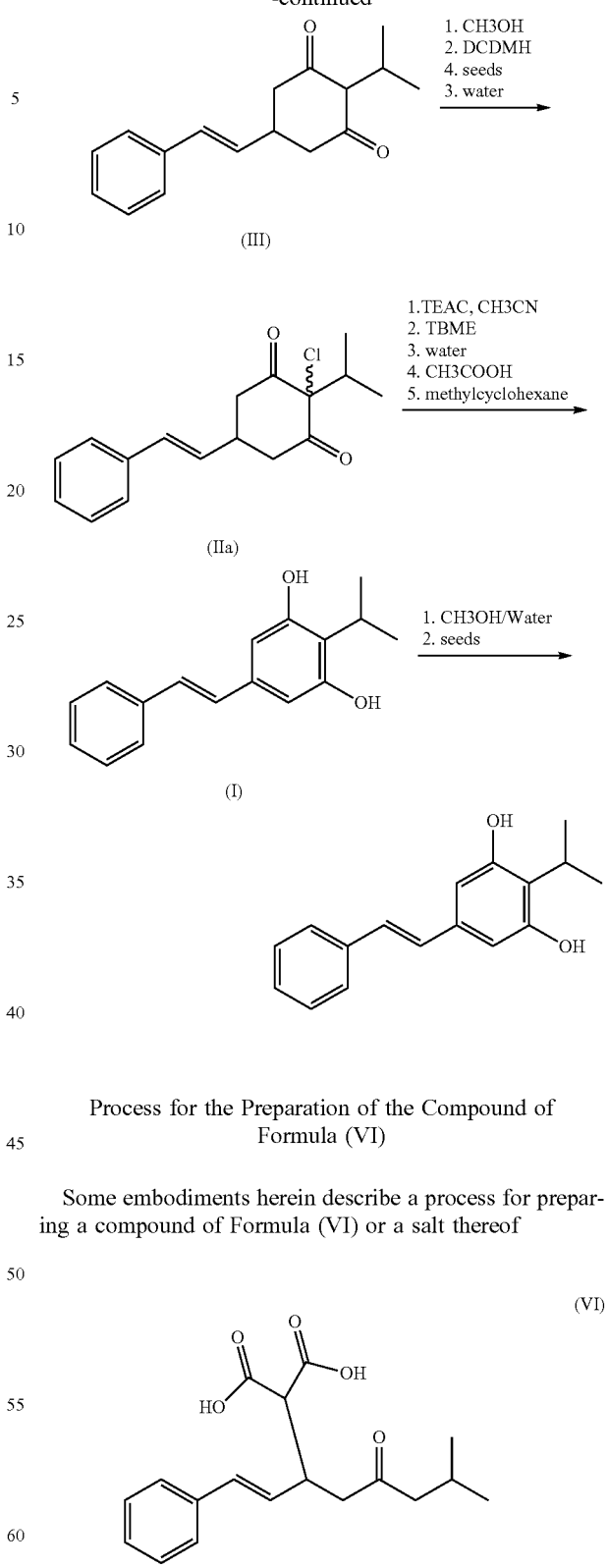
Process for the Preparation of the Compound of Formula (VI)
Some embodiments herein describe a process for preparing a compound of Formula (VI) or a salt thereof
comprising:
a) condensing trans-cinnamaldehyde or a salt thereof or a salt thereof with methyl isobutyl ketone to form a compound of Formula (VIII) or a salt thereof

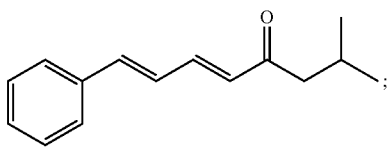
(VIII)

b) adding diethyl malonate to the compound of Formula (VIII) or a salt thereof to form a compound of Formula (VIIa) or a salt thereof

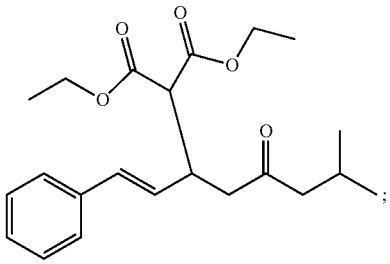
(VIIa)

and c) hydrolyzing the compound of Formula (VIIa) or a salt thereof to form the compound of Formula (VI) or a salt thereof.

In some embodiments the condensing in step a) comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step a) comprises treating the methyl isobutyl ketone with the trans-cinnamaldehyde or a salt thereof in the presence of sodium hydroxide in methanol. In some embodiments, the adding in step b) comprises contacting the diethyl malonate with the compound of Formula (VIIIa) or a salt thereof in the presence of lithium bromide/triethylamine.

Process for the Preparation of the Compound of Formula (V)

Some embodiments herein describe a process for preparing a compound of Formula (V) or a salt thereof

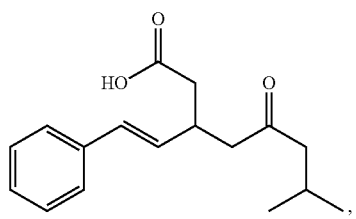
(V)

comprising decarboxylating a compound of Formula (VI) or a salt thereof

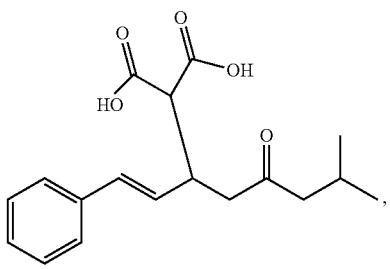
(VI)

in the presence of a base, to form the compound of Formula (V) or a salt thereof. In some embodiments the base is selected from imidazole, pyridine, and lutidine (2,6-dimethylpyridine). In some embodiments the base is trimethylamine. In some embodiments the decarboxylating comprises heating the compound of Formula (VI) or a salt thereof in the presence of trimethylamine. In some embodiments the compound of Formula (VI) or a salt thereof is prepared by any process described herein. In some embodiments the compound of Formula (VI) or a salt thereof is prepared by a process comprising:

a) condensing trans-cinnamaldehyde or a salt thereof with methyl isobutyl ketone to form a compound of Formula (VIII) or a salt thereof

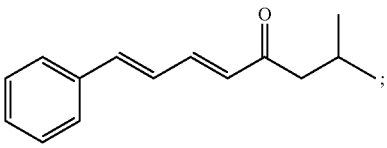
(VIII)

b) adding diethyl malonate to the compound of Formula (VIII) or a salt thereof to form a compound of Formula (VIIa) or a salt thereof

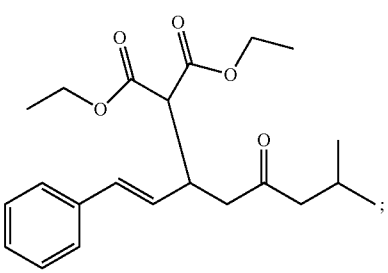
(VIIa)

and c) hydrolyzing the compound of Formula (VIIa) or a salt thereof to form the compound of Formula (VI) or a salt thereof.

Some embodiments herein describe a process for preparing a compound of Formula (V) or a salt thereof

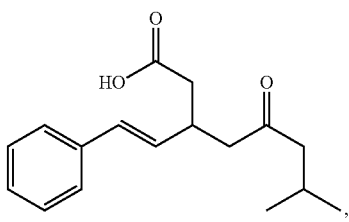

comprising:
  a) condensing trans-cinnamaldehyde or a salt thereof with methyl isobutyl ketone to form a compound of Formula (VIII) or a salt thereof

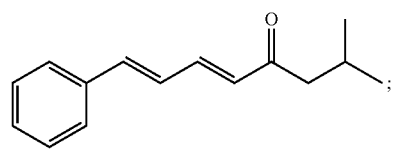

b) adding diethyl malonate to the compound of Formula (VIII) or a salt thereof to form a compound of Formula (VIIa) or a salt thereof

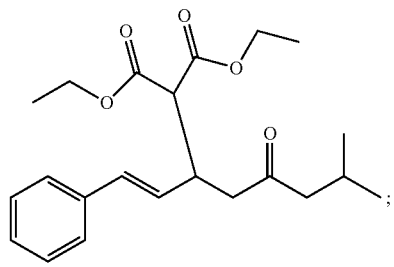

c) hydrolyzing the compound of Formula (VIIa) or a salt thereof to form the compound of Formula (VI) or a salt thereof

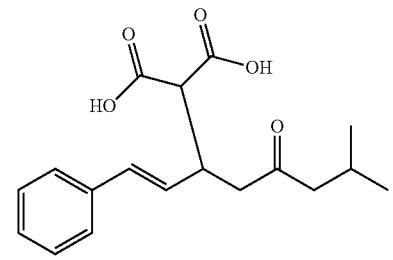

and
  d) decarboxylating the compound of Formula (VI) or a salt thereof, in the presence of a base, to form the compound of Formula (V) or a salt thereof.

In some embodiments the condensing in step a) comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step a) comprises treating the methyl isobutyl ketone with the trans-cinnamaldehyde or a salt thereof in the presence of sodium hydroxide in methanol. In some embodiments, the adding in step b) comprises contacting the diethyl malonate with the compound of Formula (VIIIa) or a salt thereof in the presence of lithium bromide/triethylamine. In some embodiments the base in step d) is selected from imidazole, pyridine, and lutidine (2,6-dimethylpyridine). In some embodiments the base in step d) is trimethylamine. In some embodiments the decarboxylating in step d) comprises heating the compound of Formula (VI) or a salt thereof in the presence of trimethylamine.

Process for the Preparation of the Compound of Formula (IVa)

Some embodiments herein describe a process for preparing a compound of Formula (IVa) or a salt thereof

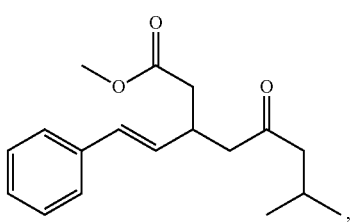

comprising esterifying a compound of Formula (V) or a salt thereof

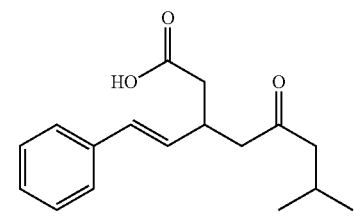

to form the compound of Formula (IVa) or a salt thereof. In some embodiments the esterifying of the compound of Formula (V) or a salt thereof is carried out using methanol and hydrochloric acid to obtain compound (IVa). In some embodiments the esterifying comprises treating the compound of Formula (V) or a salt thereof with aqueous hydrochloric acid in methanol. In some embodiments the compound of Formula (V) or a salt thereof or a salt thereof, is prepared by any method described herein. In some embodiments the compound of Formula (V) or a salt thereof is prepared by a process comprising decarboxylating a compound of Formula (VI) or a salt thereof (VI)

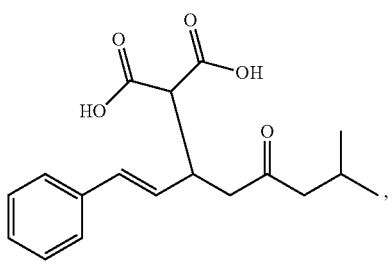

in the presence of a base, to form the compound of Formula (V) or a salt thereof. In some embodiments the compound of Formula (VI) or a salt thereof is prepared by any process described herein. In some embodiments the compound of Formula (VI) or a salt thereof is prepared by a process comprising:

i. condensing trans-cinnamaldehyde or a salt thereof or a salt thereof with methyl isobutyl ketone to form a compound of Formula (VIII) or a salt thereof (VIII)

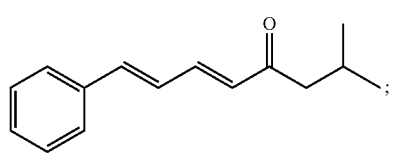

ii. adding diethyl malonate to the compound of Formula (VIII) or a salt thereof to form a compound of Formula (VIIa) or a salt thereof (VIIa)

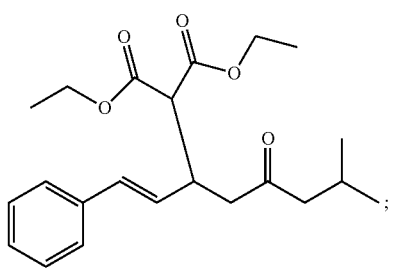

and
iii. hydrolyzing the compound of Formula (VIIa) or a salt thereof to form the compound of Formula (VI) or a salt thereof.

Some embodiments herein describe a process for preparing a compound of Formula (IVa) or a salt thereof (IVa)

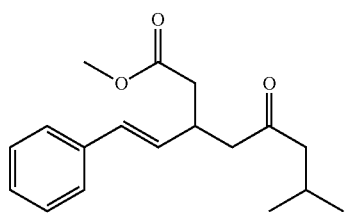

comprising:
a) condensing trans-cinnamaldehyde or a salt thereof with methyl isobutyl ketone to form a compound of Formula (VIII) or a salt thereof (VIII)

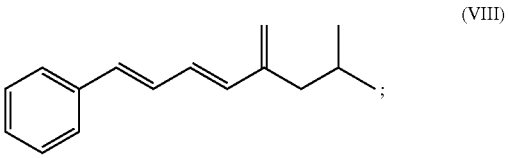 [SMILES: C=C(/C=C/C=C/c1ccccc1)CC(C)C]

b) adding diethyl malonate to the compound of Formula (VIII) or a salt thereof to form a compound of Formula (VIIa) or a salt thereof (VIIa)

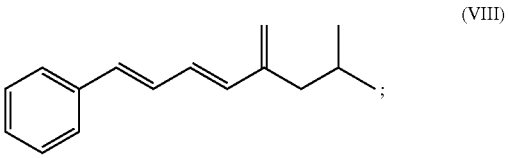 [SMILES: C=C(/C=C/C=C/c1ccccc1)CC(C)C]

c) hydrolyzing the compound of Formula (VIIa) or a salt thereof to form the compound of Formula (VI) or a salt thereof (VI)

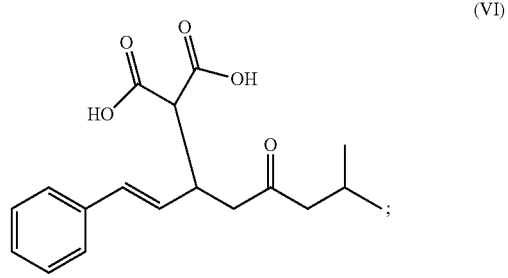 [SMILES: CC(C)CC(=O)CC(/C=C/c1ccccc1)CC(C(=O)O)C(=O)O]

d) decarboxylating the compound of Formula (VI) or a salt thereof, in the presence of a base, to form the compound of Formula (V) or a salt thereof (V)

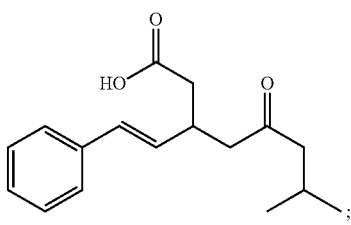

and
e) esterifying a compound of Formula (V) or a salt thereof to form the compound of Formula (IVa) or a salt thereof.

In some embodiments the condensing in step a) comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step a) comprises treating the methyl isobutyl ketone with the trans-cinnamaldehyde or a salt thereof in the presence of sodium hydroxide in methanol. In some embodiments, the adding in step b) comprises contacting the diethyl malonate with the compound of Formula (VIIIa) or a salt thereof in the presence of lithium bromide/triethylamine. In some embodiments the base in step d) is selected from imidazole, pyridine, and lutidine (2,6-dimethylpyridine). In some embodiments the base in step d) is trimethylamine. In some embodiments the decarboxylating in step d) comprises heating the compound of Formula (VI) or a salt thereof in the presence of trimethylamine. In some embodiments the esterifying of the compound of Formula (V) or a salt thereof in step e) is carried out using methanol and hydrochloric acid to obtain compound (IVa). In some embodiments the esterifying in step e) comprises treating the compound of Formula (V) or a salt thereof with aqueous hydrochloric acid in methanol.

Process for the Preparation of the Compound of Formula (IIa)

Some embodiments herein describe a process for preparing a compound of Formula (IIa) or a salt thereof

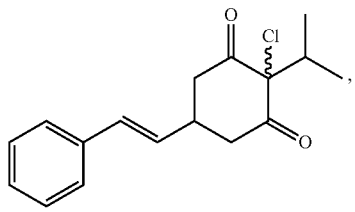

(IIa)

comprising halogenating a compound of Formula (III) or a salt thereof

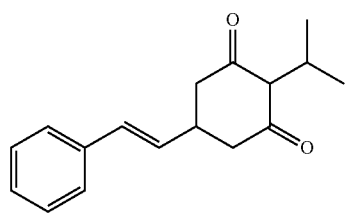

(III)

to form the compound of Formula (IIa) or a salt thereof. In some embodiments the halogenating comprises treating the compound of Formula (III) or a salt thereof with a halogenating agent. In some embodiments the halogenating agent is selected from 1,3-dichloro-5,5-dimethylhydantoin (DCDMH); N-chlorosuccinimide (NCS); and trichloroisocyanuric acid (TCCA). In some embodiments the halogenating agent is DCDMH. In some embodiments, the compound of Formula (III) or a salt thereof is prepared by any process described herein. In some embodiments, the compound of Formula (III) or a salt thereof is prepared by a process comprising cyclizing a compound of Formula (IVa) or a salt thereof

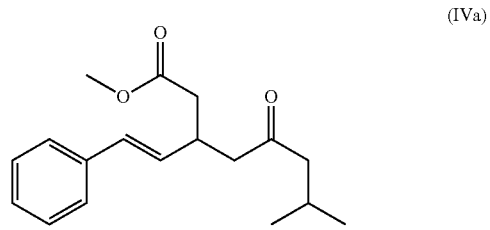

(IVa)

to form the compound of Formula (III) or a salt thereof. In some embodiments the compound of Formula (IVa) or a salt thereof is prepared by any process described herein. In some embodiments the compound of Formula (IVa) or a salt thereof is prepared by a process comprising esterifying a compound of Formula (V) or a salt thereof

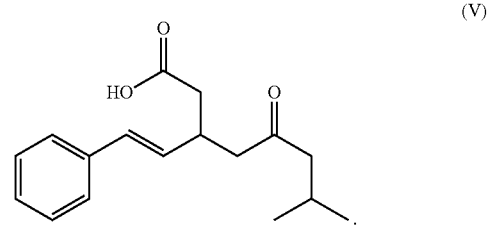 [SMILES: CC(C)CC(=O)CC(/C=C/c1ccccc1)CC(=O)O]

(V)

In some embodiments the compound of Formula (V) or a salt thereof is prepared by any process described herein. In some embodiments the compound of Formula (V) or a salt thereof is prepared by a process comprising decarboxylating a compound of Formula (VI) or a salt thereof

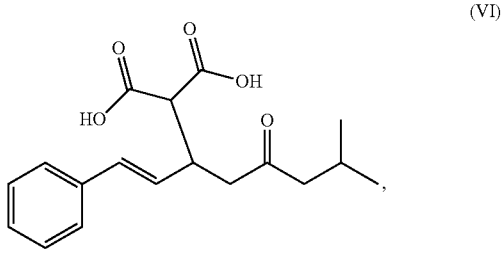 [SMILES: CC(C)CC(=O)CC(/C=C/c1ccccc1)C(C(=O)O)C(=O)O]

(VI)

in the presence of a base, to form the compound of Formula (V) or a salt thereof. In some embodiments the compound of Formula (VI) or a salt thereof is prepared by any process described herein. In some embodiments the compound of Formula (VI) or a salt thereof is prepared by a process comprising:

i. condensing trans-cinnamaldehyde or a salt thereof with methyl isobutyl ketone to form a compound of Formula (VIII) or a salt thereof

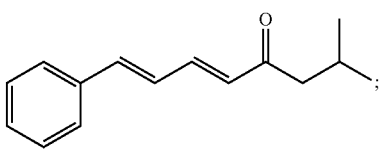 (VIII)

ii. adding diethyl malonate to the compound of Formula (VIII) or a salt thereof to form a compound of Formula (VIIa) or a salt thereof

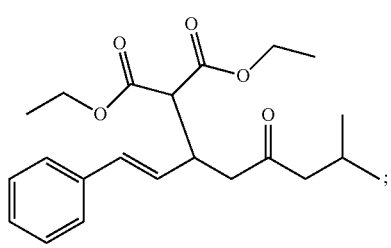 (VIIa)

and iii. hydrolyzing the compound of Formula (VIIa) or a salt thereof to form the compound of Formula (VI) or a salt thereof.

Some embodiments herein describe a process for preparing a compound of Formula (IIa) or a salt thereof

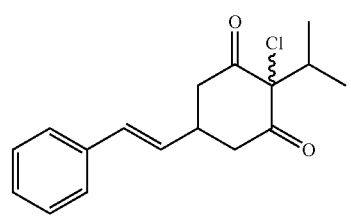 (IIa)

comprising:

a) condensing trans-cinnamaldehyde or a salt thereof with methyl isobutyl ketone to form a compound of Formula (VIII or a salt thereof

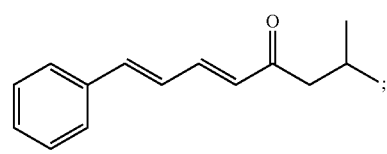 (VIII)

b) adding diethyl malonate to the compound of Formula (VIII) or a salt thereof to form a compound of Formula (VIIa) or a salt thereof

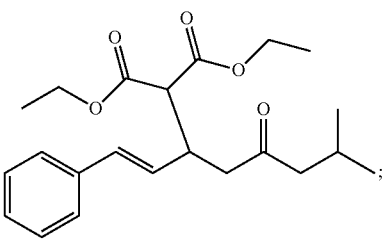 (VIIa)

c) hydrolyzing the compound of Formula (VIIa) or a salt thereof to form the compound of Formula (VI) or a salt thereof

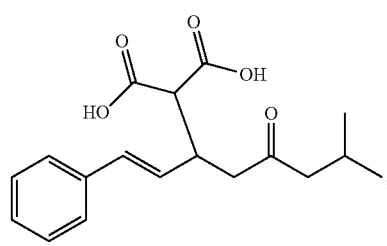 (VI)

d) decarboxylating the compound of Formula (VI) or a salt thereof, in the presence of a base, to form the compound of Formula (V) or a salt thereof

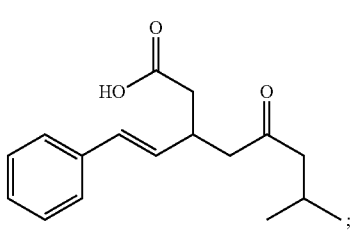 (V)

e) esterifying a compound of Formula (V) or a salt thereof to form the compound of Formula (IVa) or a salt thereof

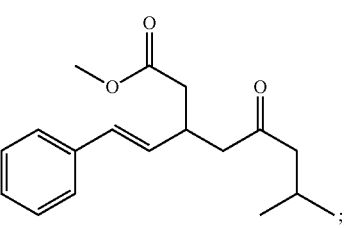 (IVa)

f) cyclizing a compound of Formula (IVa) or a salt thereof to form the compound of Formula (III) or a salt thereof

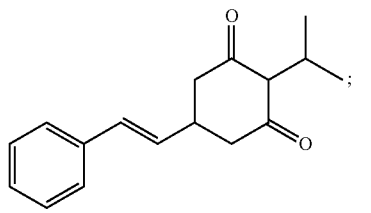
(III)

and
   g) halogenating a compound of Formula (III) or a salt thereof to form the compound of Formula (IIa) or a salt thereof.

In some embodiments the condensing in step a) comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step a) comprises treating the methyl isobutyl ketone with the trans-cinnamaldehyde or a salt thereof in the presence of sodium hydroxide in methanol. In some embodiments, the adding in step b) comprises contacting the diethyl malonate with the compound of Formula (VIIIa) or a salt thereof in the presence of lithium bromide/triethylamine. In some embodiments the base in step d) is selected from imidazole, pyridine, and lutidine (2,6-dimethylpyridine). In some embodiments the base in step d) is trimethylamine. In some embodiments the decarboxylating in step d) comprises heating the compound of Formula (VI) or a salt thereof in the presence of trimethylamine. In some embodiments the esterifying of the compound of Formula (V) or a salt thereof in step e) is carried out using methanol and hydrochloric acid to obtain compound (IVa). In some embodiments the esterifying in step e) comprises treating the compound of Formula (V) or a salt thereof with aqueous hydrochloric acid in methanol. In some embodiments the halogenating in step g) comprises treating the compound of Formula (III) or a salt thereof with a halogenating agent. In some embodiments the halogenating agent is selected from 1,3-dichloro-5,5-dimethylhydantoin (DCDMH); N-chlorosuccinimide (NCS); and trichloroisocyanuric acid (TCCA). In some embodiments the halogenating agent is DCDMH.

Compound of Formula (I) Prepared by Process A

Some embodiments herein describe a compound of Formula (I) or a salt or solvate thereof

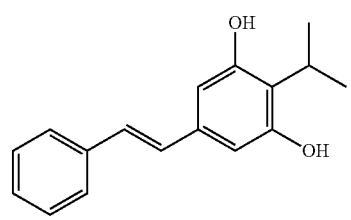
(I)

prepared by a process comprising:
   a) decarboxylating a compound of Formula (VI) or a salt thereof

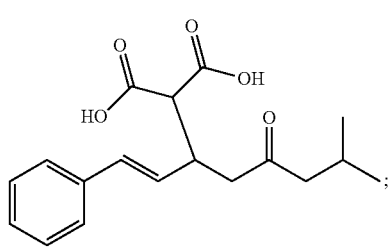
(VI)

to form a compound of Formula (V) or a salt thereof

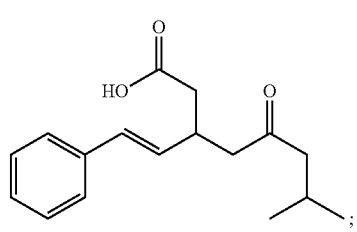
(V)

b) esterifying the compound of Formula (V) or a salt thereof to form a compound of Formula (IV) or a salt thereof

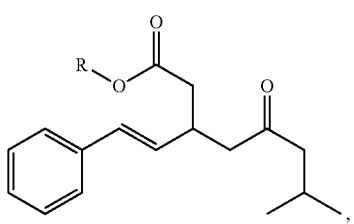
(IV)

wherein R is $C_{1-4}$ alkyl;
   c) cyclizing the compound of Formula (IV) or a salt thereof to form a compound of Formula (III) or a salt thereof

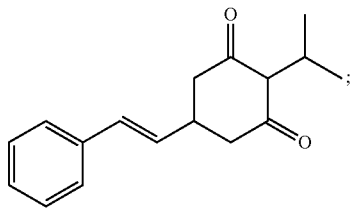
(III)

d) halogenating the compound of Formula (III) or a salt thereof to form a compound of Formula (II) or a salt thereof

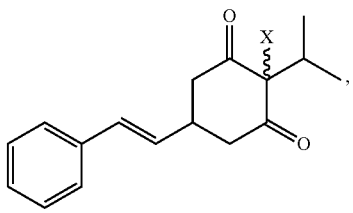

(II)

wherein X is selected from Br, Cl and I; and e) aromatizing the compound of Formula (II) or a salt thereof to form the compound of Formula (I) or a salt or solvate thereof.

Some embodiments describe the compound of Formula (I) or a salt or solvate thereof wherein the process further comprises isolating the compound of Formula (III) or a salt thereof. Some embodiments describe the compound of Formula (I) or a salt or solvate thereof wherein the process comprises isolating the compound of Formula (II) or a salt thereof. Some embodiments describe the compound of Formula (I) or a salt or solvate thereof wherein the process further comprises purifying the compound of Formula I obtained from step e). In some embodiments the purifying comprises crystallization of Formula (I). In some embodiments the compound of Formula (I) is crystal form 1. In some embodiments the compound of Formula (I) is an anhydrous crystal. In some embodiments the compound of Formula (I) has an X-ray powder diffraction pattern substantially as shown in FIG. 1. In some embodiments the compound of Formula (I) is in a crystalline solid state characterised by an X-ray powder diffraction (XRPD) pattern with specific peaks at 15.0, 17.8, 19.1, 20.2, 21.5, 22.4, 23.3, 24.5, 26.2 and 27.9 degrees (all values±0.1° 2θ experimental error). In some embodiments the compound of Formula (I) is in a crystalline solid state characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees (all values±0.1° 2θ experimental error). In some embodiments the compound of Formula (I) is an acetic acid solvate in crystalline solid state form. In some embodiments, the compound of Formula (I) is an acetic acid solvate in crystalline solid state form which has an X-ray powder diffraction pattern substantially as shown in FIG. 2. In another embodiment the compound of Formula (I) is an acetic acid solvate in crystalline solid state characterised by an X-ray powder diffraction (XRPD) pattern with specific peaks at 6.7, 10.2, 11.1, 15.4, 16.9, 17.2, and 24.8 degrees (all 2θ values, ±0.1° 2θ experimental error). In another embodiment the compound of Formula (I) is an acetic acid solvate in crystalline solid state characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees (all 2θ values, ±0.1° 2θ experimental error).

In some embodiments the decarboxylating of the compound of Formula (VI) or a salt thereof in step a) comprises the presence of a base. In some embodiments the base is selected from imidazole, pyridine, and lutidine (2,6-dimethylpyridine). In some embodiments the base is trimethylamine. In some embodiments the decarboxylating comprises heating the compound of Formula (VI) or a salt thereof in the presence of trimethylamine.

In some embodiments R of the compound of Formula (IV) or a salt thereof in step b) is selected from the group consisting of methyl, ethyl, propyl, or butyl. In some embodiments R of the compound of Formula (IV) or a salt thereof in step b) is t-butyl. In some embodiments R of the compound of Formula (IV) or a salt thereof in step b) is methyl. In some embodiments the esterifying of the compound of Formula (V) or a salt thereof in step b) is carried out using methanol and hydrochloric acid to obtain compound (IV). In some embodiments the esterifying comprises treating the compound of Formula (V) or a salt thereof with aqueous hydrochloric acid in methanol.

In some embodiments the cyclization in step c) comprises contacting the compound of Formula (IV) or salt thereof, with a base. In some embodiments the cyclization is performed using potassium tert-butoxide. In some embodiments the cyclization is carried out in 2-methyltetrahydrofuran. In some embodiments the cyclization comprises treating a compound of Formula (IV) or a salt thereof, for example a compound of (IVa) or a salt thereof, with potassium tert-butoxide in 2-methyltetrahydrofuran. In some embodiments the compound of Formula (III) or a salt thereof is further acidified and isolated by precipitation with methylcyclohexane.

In some embodiments X of the compound of Formula (II) or a salt thereof in step d) is Cl, Br, or I. In some embodiments X of the compound of Formula (II) or a salt thereof in step d) is Cl. In some embodiments the halogenating comprises treating the compound of Formula (III) or a salt thereof with a halogenating agent. In some embodiments the halogenating agent is selected from 1,3-dichloro-5,5-dimethylhydantoin (DCDMH); N-chlorosuccinimide (NCS); and trichloroisocyanuric acid (TCCA). In some embodiments the halogenating agent is DCDMH and the compound of Formula (II) or a salt thereof is a compound of Formula (IIa) or a salt thereof.

In some embodiments the aromatizing in step e) is carried out in a suitable solvent and optionally with an additive reagent. In some embodiments the aromatizing in step e) is carried out in a suitable solvent which is a polar aprotic solvent selected from the group consisting of dimethylformamide (DMF), 1,3-dimethyl-3,4,5,6-tetrahydro-2(1H)-pyrimidinone. In some embodiments the aromatizing in step e) is carried out in the presence of an additive reagent in a solvent selected from the group consisting of acetonitrile, toluene, 2-methyl tetrahydrofuran, isopropyl acetate, acetone and methyl isobutyl ketone. In some embodiments the aromatizing is carried out in acetonitrile in the presence of an additive reagent. In some embodiments the additive reagent is a quaternary ammonium salt. In some embodiments the quaternary ammonium salt is selected from the group consisting of tetrabutylammonium bromide, benzyltriethylammonium chloride, tetrabutylammonium chloride, tetraethylammonium chloride and tetramethylammonium chloride. In some embodiments the quaternary ammonium salt is tetraethylammonium chloride. In some embodiments the aromatizing is carried out in acetonitrile with tetraetylammonium chloride.

In some embodiments R of step b) is methyl and X of step d) is chloro.

Some embodiments describe the compound of Formula (I) or a salt thereof wherein the compound of Formula (VI) or a salt thereof is prepared by any process described herein. Some embodiments describe the compound of Formula (I) or a salt or solvate thereof wherein the compound of Formula (VI) or a salt thereof is prepared by a process comprising:

i. condensing trans-cinnamaldehyde or a salt thereof with methyl isobutyl ketone to form a compound of Formula (VIII) or a salt thereof

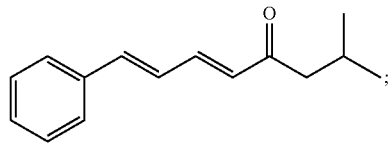

(VIII)

ii. adding a dialkyl malonic ester of the Formula R₁O(O)C—CH₂—C(O)OR₂, wherein each of R₁ and R₂ is independently C₁₋₄ alkyl, to the compound of Formula (VIII) or a salt thereof to form a compound of Formula (VII) or a salt thereof

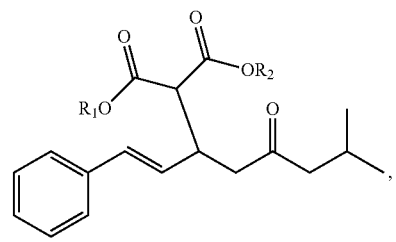

(VII)

wherein each R₁ and R₂ are as defined for the dialkyl malonic ester;

iii. hydrolyzing the compound of Formula (VII) or a salt thereof to form the compound of Formula (VI) or a salt thereof.

In some embodiments the condensing in step i. comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step i. comprises treating the methyl isobutyl ketone with the trans-cinnamaldehyde or a salt thereof in the presence of sodium hydroxide in methanol.

In some embodiments each of $R^1$ and $R^2$ in step ii. is ethyl. In some embodiments the dialkyl malonic ester in step ii. is di-tert-butylmalonate or diethyl malonate. In some embodiments, the adding in step ii. comprises contacting the malonic ester with the compound of Formula (VIII) or a salt thereof in the presence of lithium bromide/triethylamine.

Compound of Formula (I) Prepared by Process B

Some embodiments herein describe a compound of Formula (I) or a salt or solvate thereof

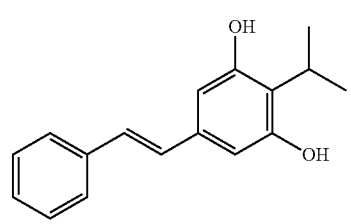

(I)

prepared by a process comprising:

a) decarboxylating a compound of Formula (VI) or a salt thereof

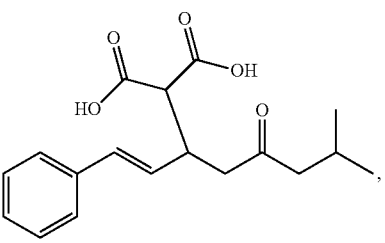

(VI)

to form a compound of Formula (V) or a salt thereof

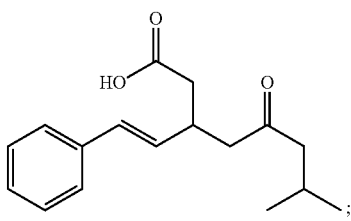

(V)

b) esterifying the compound of Formula (V) or a salt thereof to form a compound of Formula (IVa) or a salt thereof

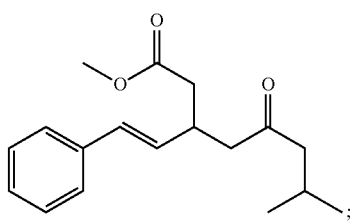

(IVa)

c) cyclizing the compound of Formula (IVa) or a salt thereof to form a compound of Formula (III) or a salt thereof

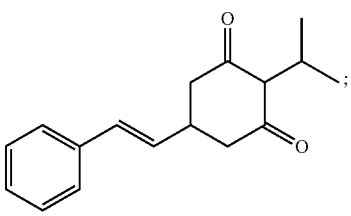

(III)

d) halogenating the compound of Formula (III) or a salt thereof to form a compound of Formula (IIa) or a salt thereof

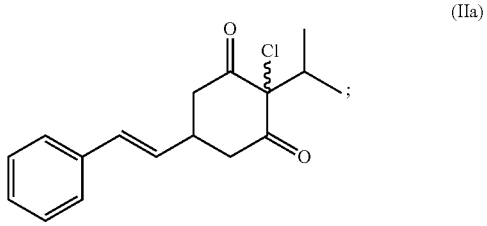

(IIa)

and e) aromatizing the compound of Formula (IIa) or a salt thereof to form the compound of Formula (I) or a salt or solvate thereof.

Some embodiments describe the compound of Formula (I) or a salt or solvate thereof wherein the process further comprises isolating the compound of Formula (III) or a salt thereof. Some embodiments describe the compound of Formula (I) or a salt or solvate thereof wherein the process comprises isolating the compound of Formula (IIa) or a salt thereof. Some embodiments describe the compound of Formula (I) or a salt or solvate thereof wherein the process further comprises purifying the compound of Formula (I) obtained from step e). In some embodiments the purifying comprises crystallization of Formula (I). In some embodiments the compound of Formula (I) is crystal form 1. In some embodiments the compound of Formula (I) is an anhydrous crystal. In some embodiments the compound of Formula (I) has an X-ray powder diffraction pattern substantially as shown in FIG. 1. In some embodiments the compound of Formula (I) is in a crystalline solid state characterised by an X-ray powder diffraction (XRPD) pattern with specific peaks at 15.0, 17.8, 19.1, 20.2, 21.5, 22.4, 23.3, 24.5, 26.2 and 27.9 degrees (all values±0.1° 2θ experimental error). In some embodiments the compound of Formula (I) is in a crystalline solid state characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees (all values±0.1° 2θ experimental error). In some embodiments the compound of Formula (I) is an acetic acid solvate in crystalline solid state form. In some embodiments, the compound of Formula (I) is an acetic acid solvate in crystalline solid state form which has an X-ray powder diffraction pattern substantially as shown in FIG. 2. In another embodiment the compound of Formula (I) is an acetic acid solvate in crystalline solid state characterised by an X-ray powder diffraction (XRPD) pattern with specific peaks at 6.7, 10.2, 11.1, 15.4, 16.9, 17.2, and 24.8 degrees (all 2θ values, ±0.1° 2θ experimental error). In another embodiment the compound of Formula (I) is an acetic acid solvate in crystalline solid state characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees (all 2θ values, ±0.1° 2θ experimental error).

In some embodiments the decarboxylating of the compound of Formula (VI) or a salt thereof in step a) comprises the presence of a base. In some embodiments the base is selected from imidazole, pyridine, and lutidine (2,6-dimethylpyridine). In some embodiments the base is trimethylamine. In some embodiments the decarboxylating comprises heating the compound of Formula (VI) or a salt thereof in the presence of trimethylamine.

In some embodiments the esterifying of the compound of Formula (V) or a salt thereof in step b) is carried out using methanol and hydrochloric acid to obtain the compound of Formula (IVa). In some embodiments the esterifying comprises treating the compound of Formula (V) or a salt thereof with aqueous hydrochloric acid in methanol.

In some embodiments the cyclization in step c) comprises contacting the compound of Formula (IVa) or salt thereof, with a base. In some embodiments the cyclization is performed using potassium tert-butoxide. In some embodiments the cyclization is carried out in 2-methyltetrahydrofuran. In some embodiments the cyclization comprises treating a compound of Formula (IVa) or a salt thereof with potassium tert-butoxide in 2-methyltetrahydrofuran. In some embodiments the compound of Formula (III) or a salt thereof is further acidified and isolated by precipitation with methylcyclohexane.

In some embodiments the halogenating in step d) comprises treating the compound of Formula (III) or a salt thereof with a halogenating agent. In some embodiments the halogenating agent is selected from 1,3-dichloro-5,5-dimethylhydantoin (DCDMH); N-chlorosuccinimide (NCS); and trichloroisocyanuric acid (TCCA). In some embodiments the halogenating agent is DCDMH.

In some embodiments the aromatizing in step e) is carried out in a suitable solvent and optionally with an additive reagent. In some embodiments the aromatizing in step e) is carried out in a suitable solvent which is a polar aprotic solvent selected from the group consisting of dimethylformamide (DMF), 1,3-dimethyl-3,4,5,6-tetrahydro-2(1H)-pyrimidinone. In some embodiments the aromatizing in step e) is carried out in the presence of an additive reagent in a solvent selected from the group consisting of acetonitrile, toluene, 2-methyl tetrahydrofuran, isopropyl acetate, acetone and methyl isobutyl ketone. In some embodiments the aromatizing is carried out in acetonitrile in the presence of an additive reagent. In some embodiments the additive reagent is a quaternary ammonium salt. In some embodiments the quaternary ammonium salt is selected from the group consisting of tetrabutylammonium bromide, benzyltriethylammonium chloride, tetrabutylammonium chloride, tetraethylammonium chloride and tetramethylammonium chloride. In some embodiments the quaternary ammonium salt is tetraethylammonium chloride. In some embodiments the aromatizing is carried out in acetonitrile with tetraetylammonium chloride.

Some embodiments describe the compound of Formula (I) or a salt thereof wherein the compound of Formula (VI) or a salt thereof is prepared by any process described herein. Some embodiments describe the compound of Formula (I) or a salt thereof wherein the compound of Formula (VI) or a salt thereof is prepared by a process comprising:

i. condensing trans-cinnamaldehyde or a salt thereof with methyl isobutyl ketone to form a compound of Formula (VIII) or a salt thereof

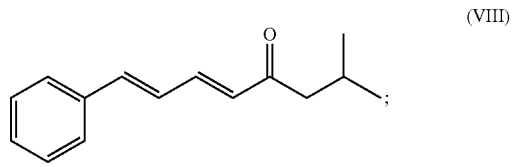 [SMILES: CC(C)CC(=O)/C=C/C=C/c1ccccc1]

(VIII)

;

ii. adding a diethyl malonic ester to the compound of Formula (VIII) or a salt thereof to form a compound of Formula (VIIa) or a salt thereof

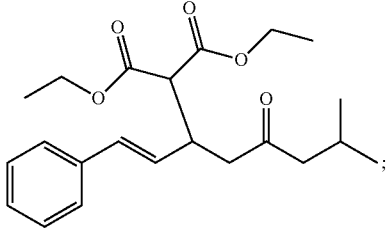

(VIIa)

and
iii. hydrolyzing the compound of Formula (VIIa) or a salt thereof to form the compound of Formula (VI) or a salt thereof.

In some embodiments the condensing in step i. comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step i. comprises treating the methyl isobutyl ketone with the trans-cinnamaldehyde or a salt thereof in the presence of sodium hydroxide in methanol.

In some embodiments, the adding in step ii. comprises contacting the diethyl malonic ester with the compound of Formula (VIII) or a salt thereof in the presence of lithium bromide/triethylamine.

Compound of Formula (I) Prepared by Process C

Some embodiments describe a compound of Formula (I) or a salt or solvate thereof

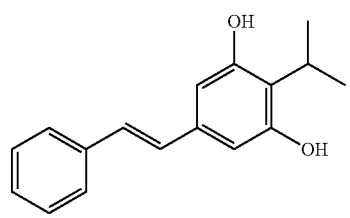

(I)

prepared by a process comprising:
a) heating a compound of Formula (VI)

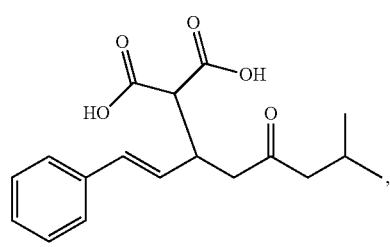

(VI)

with catalytic triethylamine to form a compound of Formula (V)

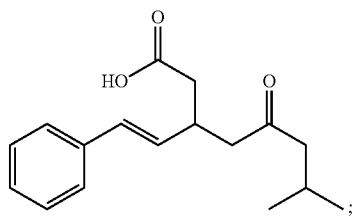

(V)

b) heating the compound of Formula (V) with methanol and aqueous hydrochloric acid to form a compound of Formula (IVa)

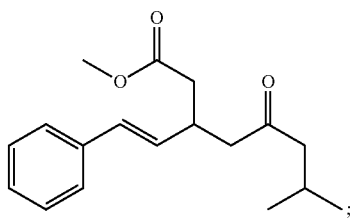

(IVa)

c) treating the compound of Formula (IVa) with potassium tert-butoxide to form a compound of Formula (III)

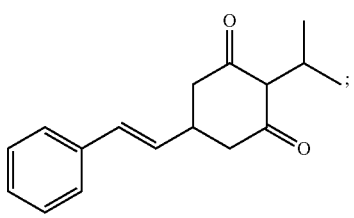

(III)

d) chlorination the compound of Formula (III) with 1,3-dichloro-5,5-dimethylhydantoin to form a compound of Formula (IIa)

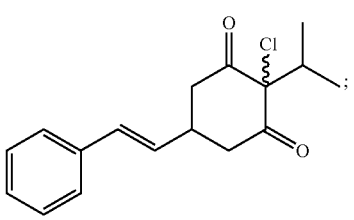

(IIa)

and
e) heating the compound of Formula (IIa) in acetonitrile with tetraethylammonium chloride to form the compound of Formula (I) or a salt or solvate thereof.

Some embodiments describe the compound of Formula (I) or a salt or solvate thereof wherein the process further comprises isolating the compound of Formula (III). Some embodiments describe the compound of Formula (I) wherein the process comprises isolating the compound of Formula (IIa). Some embodiments describe the compound of Formula (I) or a salt or solvate thereof wherein the process further comprises purifying the compound of Formula (I) obtained from step e). In some embodiments the purifying comprises crystallization of Formula (I). In some embodiments the compound of Formula (I) is crystal form 1. In some embodiments the compound of Formula (I) is an anhydrous crystal. In some embodiments the compound of Formula (I) has an X-ray powder diffraction pattern substantially as shown in FIG. 1. In some embodiments the compound of Formula (I) is in a crystalline solid state characterised by an X-ray powder diffraction (XRPD) pattern with specific peaks at 15.0, 17.8, 19.1, 20.2, 21.5, 22.4, 23.3, 24.5, 26.2 and 27.9 degrees (all values±0.1° 2θ experimental error). In some embodiments the compound of Formula (I) is in a crystalline solid state characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees (all values±0.1° 2θ experimental error). In some embodiments the compound of Formula (I) is an acetic acid solvate in crystalline solid state form. In some embodiments, the compound of Formula (I) is an acetic acid solvate in crystalline solid state form which has an X-ray powder diffraction pattern substantially as shown in FIG. 2. In another embodiment the compound of Formula (I) is an acetic acid solvate in crystalline solid state characterised by an X-ray powder diffraction (XRPD) pattern with specific peaks at 6.7, 10.2, 11.1, 15.4, 16.9, 17.2, and 24.8 degrees (all 2θ values, ±0.1° 2θ experimental error). In another embodiment the compound of Formula (I) is an acetic acid solvate in crystalline solid state characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees (all 2θ values, ±0.1° 2θ experimental error).

Some embodiments describe the compound of Formula (I) or a salt thereof wherein the compound of Formula (VI) or a salt thereof is prepared by any process described herein. Some embodiments describe the compound of Formula (I) or a salt or solvate thereof wherein the compound of Formula (VI) is prepared by a process comprising:

i. treating methyl isobutyl ketone with trans-cinnamaldehyde in the presence of methanolic sodium hydroxide to form a compound of Formula (VIII)

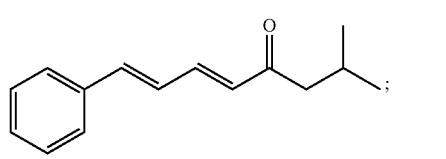

ii. treating the compound of Formula (VIII) with diethyl malonate in the presence of lithium bromide and triethylamine to form a compound of Formula (VIIa)

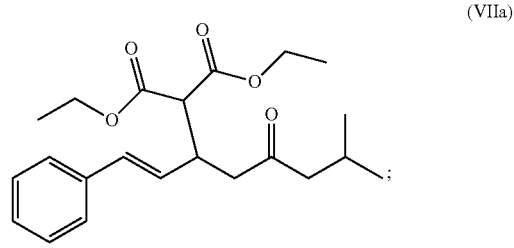 [SMILES: CCOC(=O)C(C(=O)OCC)C(/C=C/c1ccccc1)CC(=O)CC(C)C]

iii. hydrolyzing the compound of Formula (VIIa) with sodium hydroxide and ethanol to form the compound of Formula (VI).

Compound of Formula (VI) Prepared by a Process

Some embodiments herein describe a compound of Formula (VI) or a salt thereof

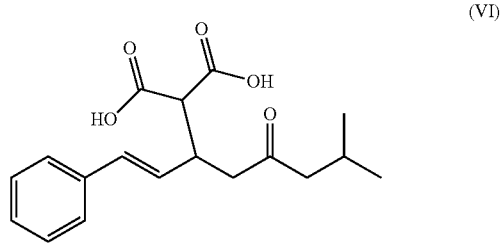 [SMILES: CC(C)CC(=O)CC(/C=C/c1ccccc1)C(C(=O)O)C(=O)O]

prepared by a process comprising:
a) condensing trans-cinnamaldehyde or a salt thereof with methyl isobutyl ketone to form a compound of Formula (VIII) or a salt thereof

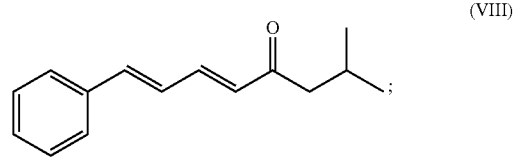 [SMILES: CC(C)CC(=O)/C=C/C=C/c1ccccc1]

b) adding diethyl malonate to the compound of Formula (VIII) or a salt thereof to form a compound of Formula (VIIa) or a salt thereof

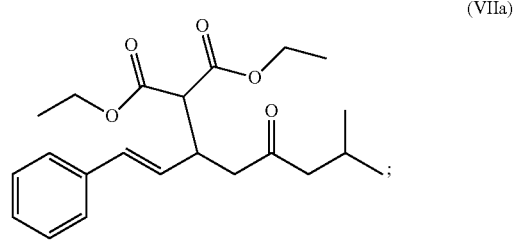 [SMILES: CCOC(=O)C(C(=O)OCC)C(/C=C/c1ccccc1)CC(=O)CC(C)C]

and
c) hydrolyzing the compound of Formula (VIIa) or a salt thereof to form the compound of Formula (VI) or a salt thereof.

In some embodiments the condensing in step a) comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step a) comprises treating the methyl isobutyl ketone with the trans-cinnamaldehyde or a salt thereof in the presence of sodium hydroxide in methanol. In some embodiments, the adding in step b) comprises contacting the diethyl malonate with the compound of Formula (VIIIa) or a salt thereof in the presence of lithium bromide/triethylamine.

Compound of Formula (V) Prepared by a Process

Some embodiments herein describe a compound of Formula (V) or a salt thereof

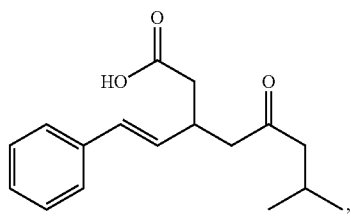
(V)

prepared by a process comprising decarboxylating a compound of Formula (VI) or a salt thereof

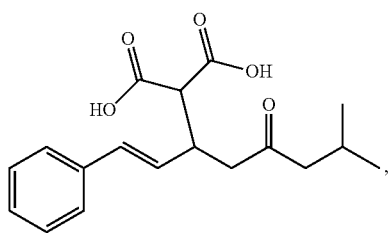
(VI)

in the presence of a base, to form the compound of Formula (V) or a salt thereof. In some embodiments the base is selected from imidazole, pyridine, and lutidine (2,6-dimethylpyridine). In some embodiments the base is trimethylamine. In some embodiments the decarboxylating comprises heating the compound of Formula (VI) or a salt thereof in the presence of trimethylamine. In some embodiments the compound of Formula (VI) or a salt thereof is prepared by any process described herein. Some embodiments describe the compound of Formula (V) or a salt thereof wherein the compound of Formula (VI) or a salt thereof is prepared by a process comprising:

i. condensing trans-cinnamaldehyde or a salt thereof with methyl isobutyl ketone to form a compound of Formula (VIII) or a salt thereof

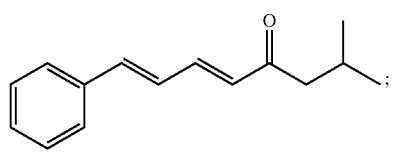
(VIII)

ii. adding diethyl malonate to the compound of Formula (VIII) or a salt thereof to form a compound of Formula (VIIa) or a salt thereof

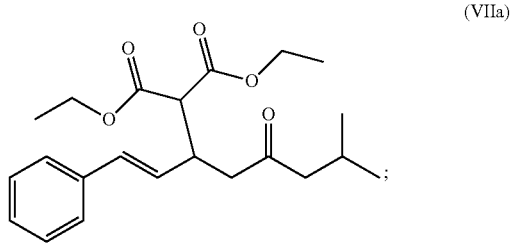 [SMILES: CCOC(=O)C(C(=O)OCC)C(/C=C/c1ccccc1)CC(=O)CC(C)C]
(VIIa)

and iii. hydrolyzing the compound of Formula (VIIa) or a salt thereof to form the compound of Formula (VI) or a salt thereof.

Some embodiments herein describe a compound of Formula (V) or a salt thereof

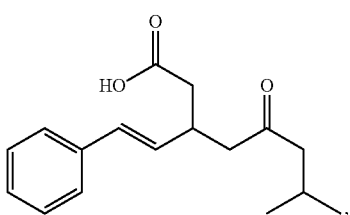
(V)

prepared by a process comprising:

a) condensing trans-cinnamaldehyde or a salt thereof with methyl isobutyl ketone to form a compound of Formula (VIII) or a salt thereof

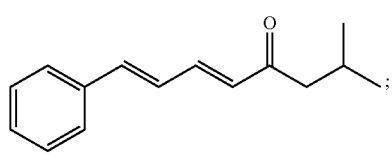
(VIII)

b) adding diethyl malonate to the compound of Formula (VIII) or a salt thereof to form a compound of Formula (VIIa) or a salt thereof

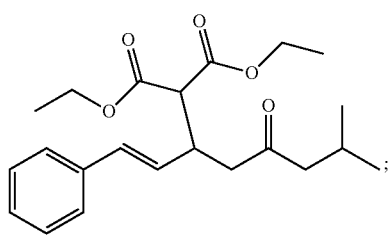
(VIIa)

c) hydrolyzing the compound of Formula (VIIa) or a salt thereof to form the compound of Formula (VI) or a salt thereof

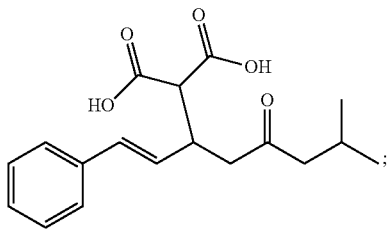
(VI)

and
d) decarboxylating the compound of Formula (VI) or a salt thereof, in the presence of a base, to form the compound of Formula (V) or a salt thereof.

In some embodiments the condensing in step a) comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step a) comprises treating the methyl isobutyl ketone with the trans-cinnamaldehyde or a salt thereof in the presence of sodium hydroxide in methanol. In some embodiments, the adding in step b) comprises contacting the diethyl malonate with the compound of Formula (VIIIa) or a salt thereof in the presence of lithium bromide/triethylamine. In some embodiments the base in step d) is selected from imidazole, pyridine, and lutidine (2,6-dimethylpyridine). In some embodiments the base in step d) is trimethylamine. In some embodiments the decarboxylating in step d) comprises heating the compound of Formula (VI) or a salt thereof in the presence of trimethylamine.

Compound of Formula (IVa) Prepared by a Process

Some embodiments herein describe a compound of Formula (IVa) or a salt thereof

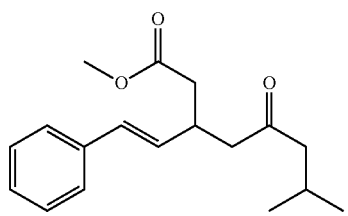
(IVa)

prepared by a process comprising esterifying a compound of Formula (V) or a salt thereof

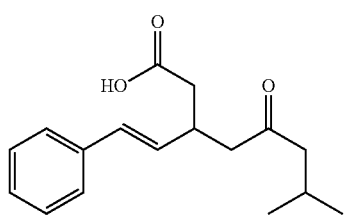
(V)

to form the compound of Formula (IVa) or a salt thereof. In some embodiments the esterifying of the compound of Formula (V) or a salt thereof is carried out using methanol and hydrochloric acid to obtain compound (IVa) or a salt thereof. In some embodiments the esterifying comprises treating the compound of Formula (V) or a salt thereof with aqueous hydrochloric acid in methanol. Some embodiments describe the compound of Formula (IVa) or a salt thereof wherein the compound of Formula (V) or a salt thereof is prepared by any process described herein. Some embodiments describe the compound of Formula (IVa) or a salt thereof wherein the compound of Formula (V) or a salt thereof is prepared by a process comprising decarboxylating a compound of Formula (VI) or a salt thereof

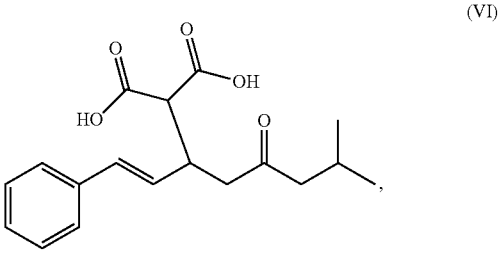 [SMILES: CC(C)CC(=O)CC(/C=C/c1ccccc1)C(C(=O)O)C(=O)O]
(VI)

in the presence of a base, to form the compound of Formula (V) or a salt thereof. Some embodiments describe the compound of Formula (IVa) or a salt thereof wherein the compound of Formula (V) or a salt thereof is prepared by any process described herein. Some embodiments describe the compound of Formula (IVa) or a salt thereof wherein the compound of Formula (V) or a salt thereof is prepared by a process comprising decarboxylating a compound of Formula (VI) or a salt thereof

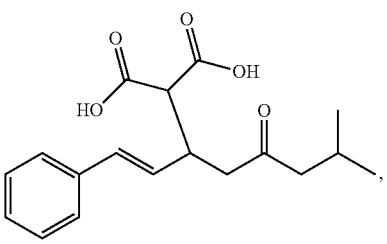
(VI)

in the presence of a base, to form the compound of Formula (V) or a salt thereof. Some embodiments describe the compound of Formula (IVa) or a salt thereof wherein the compound of Formula (VI) or a salt thereof is prepared by any process described herein. Some embodiments describe the compound of Formula (IVa) or a salt thereof wherein the compound of Formula (VI) or a salt thereof is prepared by a process comprising:
i. condensing trans-cinnamaldehyde or a salt thereof with methyl isobutyl ketone to form a compound of Formula (VIII) or a salt thereof

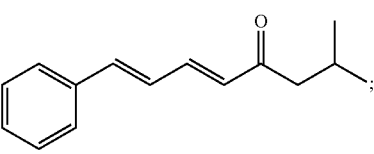
(VIII)

ii. adding diethyl malonate to the compound of Formula (VIII) or a salt thereof to form a compound of Formula (VIIa) or a salt thereof

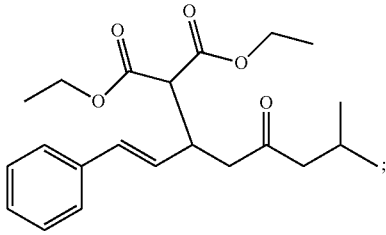
(VIIa)

and iii. hydrolyzing the compound of Formula (VIIa) or a salt thereof to form the compound of Formula (VI) or a salt thereof.

Some embodiments herein describe a compound of Formula (IVa) or a salt thereof

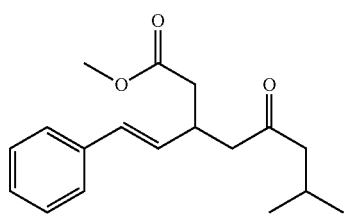
(IVa)

prepared by a process comprising:
a) condensing trans-cinnamaldehyde or a salt thereof with methyl isobutyl ketone to form a compound of Formula (VIII) or a salt thereof

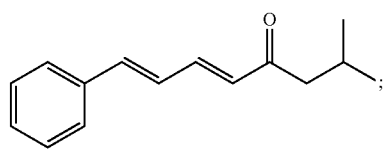
(VIII)

b) adding diethyl malonate to the compound of Formula (VIII) or a salt thereof to form a compound of Formula (VIIa) or a salt thereof

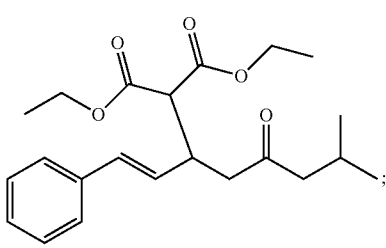
(VIIa)

c) hydrolyzing the compound of Formula (VIIa) or a salt thereof to form the compound of Formula (VI) or a salt thereof

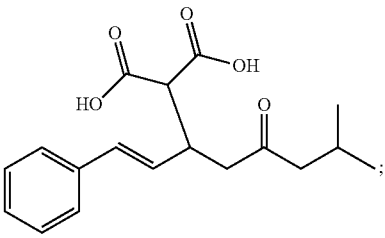
(VI)

d) decarboxylating the compound of Formula (VI) or a salt thereof, in the presence of a base, to form the compound of Formula (V) or a salt thereof

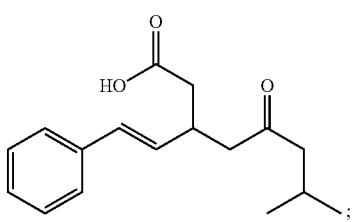
(V)

and e) esterifying a compound of Formula (V) or a salt thereof to form the compound of Formula (IVa) or a salt thereof.

In some embodiments the condensing in step a) comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step a) comprises treating the methyl isobutyl ketone with the trans-cinnamaldehyde or a salt thereof in the presence of sodium hydroxide in methanol. In some embodiments, the adding in step b) comprises contacting the diethyl malonate with the compound of Formula (VIIIa) or a salt thereof in the presence of lithium bromide/triethylamine. In some embodiments the base in step d) is selected from imidazole, pyridine, and lutidine (2,6-dimethylpyridine). In some embodiments the base in step d) is trimethylamine. In some embodiments the decarboxylating in step d) comprises heating the compound of Formula or a salt thereof VI in the presence of trimethylamine. In some embodiments the esterifying of the compound of Formula (V) or a salt thereof in step e) is carried out using methanol and hydrochloric acid to obtain compound (IVa). In some embodiments the esterifying in step e) comprises treating the compound of Formula (V) or a salt thereof with aqueous hydrochloric acid in methanol.

Compound of Formula (IIa) Prepared by a Process

Some embodiments herein describe a compound of Formula (IIa) or a salt thereof

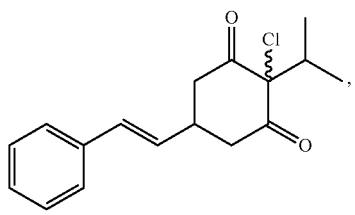
(IIa)

prepared by a process comprising halogenating a compound of Formula (III) or a salt thereof

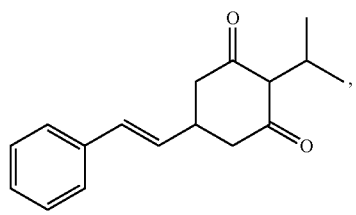
(III)

to form the compound of Formula (IIa) or a salt thereof. In some embodiments the halogenating comprises treating the compound of Formula (III) or a salt thereof with a halogenating agent. In some embodiments the halogenating agent is selected from 1,3-dichloro-5,5-dimethylhydantoin (DCDMH); N-chlorosuccinimide (NCS); and trichloroisocyanuric acid (TCCA). Some embodiments describe the compound of Formula (IIa) or a salt thereof wherein the compound of Formula (III) or a salt thereof is prepared by any process described herein. Some embodiments describe the compound of Formula (IIa) or a salt thereof wherein the compound of Formula (III) or a salt thereof is prepared by a process comprising cyclizing a compound of Formula (IVa) or a salt thereof

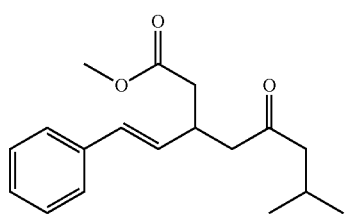
(IVa)

to form the compound of Formula (III) or a salt thereof. Some embodiments describe the compound of Formula (IIa) or a salt thereof wherein the compound of Formula (IVa) or a salt thereof is prepared by any process described herein. Some embodiments describe the compound of Formula (IIa) or a salt thereof wherein the compound of Formula (IVa) or a salt thereof is prepared by a process comprising esterifying a compound of Formula (V) or a salt thereof

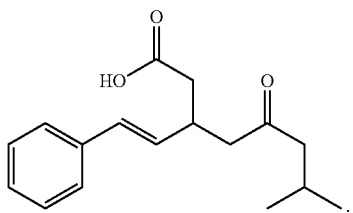
(V)

Some embodiments describe the compound of Formula (IIa) or a salt thereof wherein the compound of Formula (V) or a salt thereof is prepared by any process described herein. Some embodiments describe the compound of Formula (IIa) or a salt thereof wherein the compound of compound of Formula (V) or a salt thereof is prepared by a process comprising decarboxylating a compound of Formula (VI) or a salt thereof

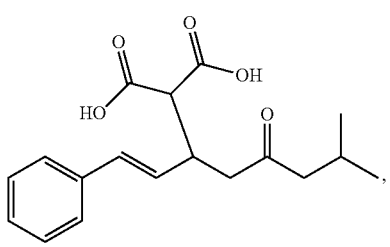
(VI)

in the presence of a base, to form the compound of Formula (V) or a salt thereof. Some embodiments describe the compound of Formula (IIa) or a salt thereof wherein the compound of Formula (VI) or a salt thereof is prepared by any process described herein. Some embodiments describe the compound of Formula (IIa) or a salt thereof wherein the compound of Formula (VI) or a salt thereof is prepared by a process comprising:

i. condensing trans-cinnamaldehyde or a salt thereof with methyl isobutyl ketone to form a compound of Formula (VIII) or a salt thereof

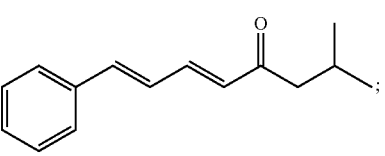
(VIII)

ii. adding diethyl malonate to the compound of Formula (VIII) or a salt thereof to form a compound of Formula (VIIa) or a salt thereof

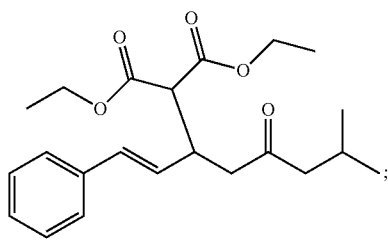

(VIIa)

and iii. hydrolyzing the compound of Formula (VIIa) or a salt thereof to form the compound of Formula (VI) or a salt thereof.

Some embodiments herein describe a compound of Formula (IIa) or a salt thereof

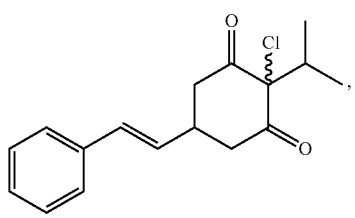

(IIa)

prepared by a process comprising:

a) condensing trans-cinnamaldehyde or a salt thereof with methyl isobutyl ketone to form a compound of Formula (VIII) or a salt thereof

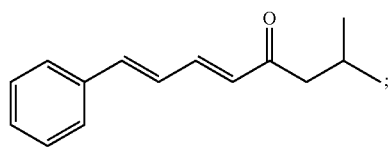

(VIII)

b) adding diethyl malonate to the compound of Formula (VIII) or a salt thereof to form a compound of Formula (VIIa) or a salt thereof

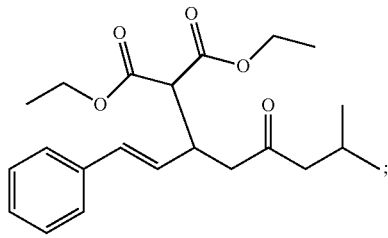

(VIIa)

c) hydrolyzing the compound of Formula (VIIa) or a salt thereof to form the compound of Formula (VI) or a salt thereof

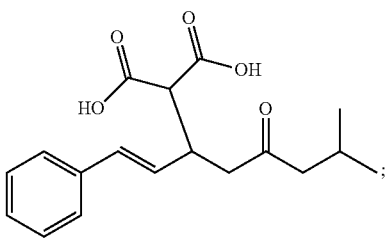

(VI)

d) decarboxylating the compound of Formula (VI) or a salt thereof, in the presence of a base, to form the compound of Formula (V) or a salt thereof

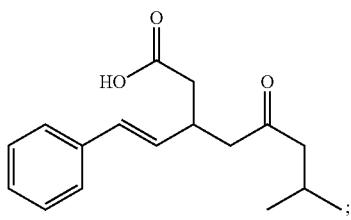

(V)

e) esterifying a compound of Formula (V) or a salt thereof to form the compound of Formula (IVa) or a salt thereof

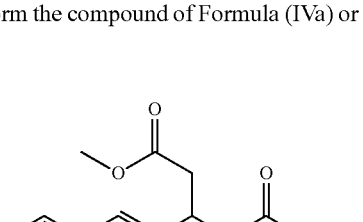

(IVa)

f) cyclizing a compound of Formula (IVa) or a salt thereof to form the compound of Formula (III) or a salt thereof

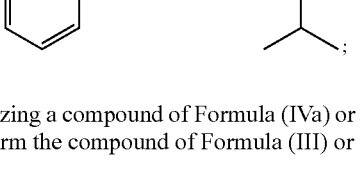

(III)

and g) halogenating the compound of Formula (III) or a salt thereof to form the compound of Formula (IIa) or a salt thereof.

In some embodiments the condensing in step a) comprises treating the methyl isobutyl ketone with the trans-cinnamaldehyde or a salt thereof in the presence of lithium, potassium or sodium hydroxide, for example the condensation is performed using potassium or sodium hydroxide in methanol. In some embodiments the condensing in step a) comprises treating the methyl isobutyl ketone with the trans-cinnamaldehyde or a salt thereof in the presence of sodium hydroxide in methanol. In some embodiments, the adding in step b) comprises contacting the diethyl malonate with the compound of Formula (VIIIa) or a salt thereof in the presence of lithium bromide/triethylamine. In some embodiments the base in step d) is selected from imidazole, pyridine, and lutidine (2,6-dimethylpyridine). In some embodiments the base in step d) is trimethylamine. In some embodiments the decarboxylating in step d) comprises heating the compound of Formula (VI) or a salt thereof in the presence of trimethylamine. In some embodiments the esterifying of the compound of Formula (V) or a salt thereof in step e) is carried out using methanol and hydrochloric acid to obtain compound (IVa). In some embodiments the esterifying in step e) comprises treating the compound of Formula (V) or a salt thereof with aqueous hydrochloric acid in methanol. In some embodiments the halogenating in step g) comprises treating the compound of Formula (III) or a salt thereof with a halogenating agent. In some embodiments the halogenating agent is selected from 1,3-dichloro-5,5-dimethylhydantoin (DCDMH); N-chlorosuccinimide (NCS); and trichloroisocyanuric acid (TCCA). In some embodiments the halogenating agent is DCDMH.

Compounds

Some embodiments describe a compound of Formula (I) in crystalline solid state form (Form 1) which has an X-ray powder diffraction pattern substantially as shown in FIG. 1. In some embodiments the compound of Formula (I) in form 1 is characterised by an X-ray powder diffraction (XRPD) pattern with specific peaks at 15.0, 17.8, 19.1, 20.2, 21.5, 22.4, 23.3, 24.5, 26.2 and 27.9 degrees (all values±0.1° 2θ experimental error). In another embodiment there the compound of Formula (I) in form 1 is characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees (all values+0.1° 2θ experimental error). In some embodiments the compound of Formula (I) is at least 80% form 1. In some embodiments the compound of Formula (I) is at least 85% form 1. In some embodiments the compound of Formula (I) is at least 90% form 1. In some embodiments the compound of Formula (I) is at least 95% form 1. In some embodiments the compound of Formula (I) is at least 99% form 1. In some embodiments the compound of Formula (I) is about 90%, about 91%, about 92%, about 93%, about 94%, about 95%, about 96%, about 97%, about 98%, or about 99% form 1.

Some embodiments describe an acetic acid solvate of the compound of Formula (I). In some embodiments, the acetic acid solvate of the compound of Formula (I) is in crystalline solid state form which has an X-ray powder diffraction pattern substantially as shown in FIG. 2. In another embodiment the acetic acid solvate of the compound of Formula (I) is characterised by an X-ray powder diffraction (XRPD) pattern with specific peaks at 6.7, 10.2, 11.1, 15.4, 16.9, 17.2, and 24.8 degrees (all 2θ values, ±0.1° 2θ experimental error). In another embodiment the acetic acid solvate of the compound of Formula (I) is characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees (all 2θ values, ±0.1° 2θ experimental error). In some embodiments the compound of Formula (I) is at least 80% acetic acid solvate of Formula (I). In some embodiments the compound of Formula (I) is at least 85% acetic acid solvate of Formula (I). In some embodiments the compound of Formula (I) is at least 90% acetic acid solvate of Formula (I). In some embodiments the compound of Formula (I) is at least 95% acetic acid solvate of Formula (I). In some embodiments the compound of Formula (I) is at least 99% acetic acid solvate of Formula (I). In some embodiments the compound of Formula (I) is about 90%, about 91%, about 92%, about 93%, about 94%, about 95%, about 96%, about 97%, about 98%, or about 99% acetic acid solvate of Formula (I).

It will be understood by one of skill in the art that the percentage of a particular form of a compound of Formula (I) is expressed in relation to all forms of Formula (I) present in a sample. For example the phrase "the compound of Formula (I) is at least 95% form 1" is meant to convey that at least 95% of all forms of the compound of Formula (I) present is in form 1. Similarly, the phrase "the compound of Formula (I) is at least 80% acetic acid solvate of Formula (I)" means that at least 80% of a sample of the compound of Formula (I) is in the form of an acetic acid solvate.

Some embodiments describe a compound of Formula (IIa) or a salt thereof

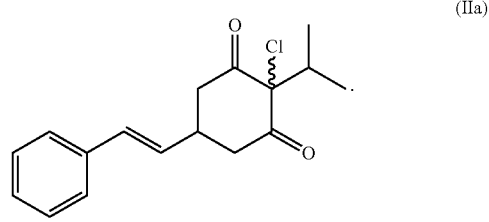 [SMILES: CC(C)C1(Cl)C(=O)CC(/C=C/c2ccccc2)CC1=O]

Some embodiments describe a compound of Formula (IVa) or a salt thereof

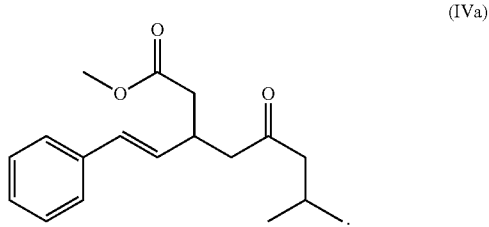 [SMILES: COC(=O)CC(/C=C/c1ccccc1)CC(=O)CC(C)C]

Some embodiments describe a compound of Formula (V) or a salt thereof

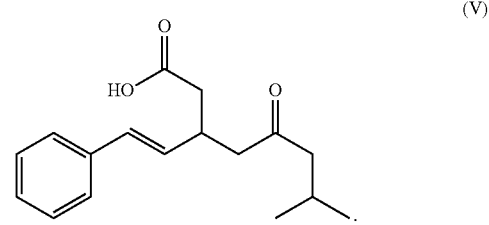 [SMILES: CC(C)CC(=O)CC(/C=C/c1ccccc1)CC(=O)O]

Some embodiments describe a compound of Formula (VI) or a salt thereof

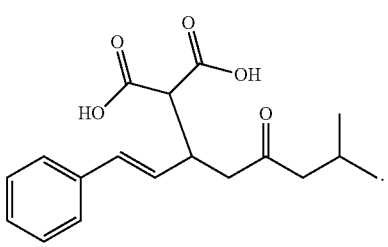
(VI)

Pharmaceutical Compositions

Embodiments herein describe a pharmaceutical composition comprising a compound of Formula (I) or a salt or solvate thereof prepared according to any embodiment described herein and a pharmaceutically acceptable excipient.

Some embodiments describe pharmaceutical composition comprising a therapeutically effective amount of compound of Formula (I) of form 1 and a pharmaceutically acceptable excipient. In some embodiments the composition of Formula (I) of form 1 is characterised by an X-ray powder diffraction (XRPD) pattern with specific peaks at 15.0, 17.8, 19.1, 20.2, 21.5, 22.4, 23.3, 24.5, 26.2 and 27.9 degrees 2θ(±0.1° 2θ). In some embodiments the compound of Formula (I) of form 1 is characterised by an X-ray powder diffraction (XRPD) pattern with at least nine, or at least eight, or at least seven, or at least six, or at least five, or at least four, or at least three specific peaks selected from 15.0, 17.8, 19.1, 20.2, 21.5, 22.4, 23.3, 24.5, 26.2 and 27.9 degrees 2θ(±0.1° 2θ). In some embodiments the compound of Formula (I) is at least 80% form 1. In some embodiments the compound of Formula (I) is at least 85% form 1. In some embodiments the compound of Formula (I) is at least 90% form 1. In some embodiments the compound of Formula (I) is at least 95% form 1. In some embodiments the compound of Formula (I) is at least 99% form 1. In some embodiments the compound of Formula (I) is about 90%, about 91%, about 92%, about 93%, about 94%, about 95%, about 96%, about 97%, about 98%, or about 99% form 1.

Some embodiments describe a pharmaceutical composition comprising a therapeutically effective amount of an acetic acid solvate of the compound of Formula (I) and a pharmaceutically acceptable excipient. In some embodiments, the acetic acid solvate of the compound of Formula (I) is in a crystalline solid state form which has an X-ray powder diffraction with specific peaks at 6.7, 10.2, 11.1, 15.4, 16.9, 17.2, and 24.8 degrees 2θ(±0.1° 2θ). In some embodiments the acetic acid solvate of a compound of Formula (I) is characterised by an X-ray powder diffraction (XRPD) pattern with at least six, or at least five, or at least four, or at least three specific peaks selected from peaks at 6.7, 10.2, 11.1, 15.4, 16.9, 17.2, and 24.8 degrees 2θ(±0.1° 2θ). In some embodiments the compound of Formula (I) is at least 80% acetic acid solvate of Formula (I). In some embodiments the compound of Formula (I) is at least 85% acetic acid solvate of Formula (I). In some embodiments the compound of Formula (I) is at least 90% acetic acid solvate of Formula (I). In some embodiments the compound of Formula (I) is at least 95% acetic acid solvate of Formula (I). In some embodiments the compound of Formula (I) is at least 99% acetic acid solvate of Formula (I). In some embodiments the compound of Formula (I) is about 90%, about 91%, about 92%, about 93%, about 94%, about 95%, about 96%, about 97%, about 98%, or about 99% acetic acid solvate of Formula (I).

Some embodiments describe a pharmaceutical composition comprising a compound of Formula (IIa) and a pharmaceutically acceptable excipient.

Some embodiments describe a pharmaceutical composition comprising a compound of Formula (IVa) and a pharmaceutically acceptable excipient.

Some embodiments describe a pharmaceutical composition comprising a compound of Formula (V) and a pharmaceutically acceptable excipient.

Some embodiments describe a pharmaceutical composition comprising a compound of Formula (VI) and a pharmaceutically acceptable excipient.

In any of the foregoing pharmaceutical compositions, the compound of Formula (I) is present in a therapeutically effective amount.

Methods of preparing pharmaceutical compositions of the compound of Formula (I) and salts and solvates thereof are familiar to those skilled in the art, which are described in Remington: The Science and Practice of Pharmacy, 21$^{st}$ Edition 2006.

In some embodiments, a compound of Formula (I) or a salt or solvate thereof prepared by any process described herein, is at least 80% pure by weight. In some embodiments, a compound of Formula (I) or a salt or solvate thereof prepared by any process described herein, is at least 85% pure by weight. In some embodiments, a compound of Formula (I) or a salt or solvate thereof prepared by any process described herein, is at least 90% pure by weight. In some embodiments, a compound of Formula (I) or a salt or solvate thereof prepared by any process described herein, is at least 95% pure by weight. In some embodiments, a compound of Formula (I) or a salt or solvate thereof prepared by any process described herein, is at least 99% pure by weight. In some embodiments, a compound of Formula (I) or a salt or solvate thereof prepared by any process described herein, is about 90%, about 91%, about 92%, about 93%, about 94%, about 95%, about 96%, about 97%, about 98%, or about 99%, pure by weight.

Definitions

The term "$C_{1-4}$ alkyl" means a straight or branched alkyl containing at least one, and at most four, carbon atoms. Examples of "$C_{1-4}$ alkyl" as used herein include, but are not limited to, methyl, ethyl, n-propyl, n-butyl, isobutyl, isopropyl and t-butyl.

References herein to compounds of specified Formulae and "salts thereof" cover the compounds as free bases, or as salts thereof, for example as pharmaceutically acceptable salts thereof. For a review of suitable pharmaceutically acceptable salts see Berge et al., J. Pharm. Sci., 66:1-19, (1977).

"Solvates" of the compounds of the specified Formulae may be formed wherein solvent molecules are incorporated into the crystalline lattice during crystallization. Solvates may involve non-aqueous solvents such as ethanol, isopropyl alcohol, N,N-dimethylsulfoxide (DMSO), acetic acid, ethanolamine, and ethyl acetate, or they may involve water as the solvent that is incorporated into the crystalline lattice.

As used herein a "pharmaceutically acceptable excipient" refers to one or more pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of Formula (I) or a pharmaceutically acceptable salt thereof when administered to a patient.

As used herein an X-ray powder diffraction pattern that is "substantially as shown in FIG. 1" or "substantially as shown in FIG. 2" relates to an X-ray powder diffraction pattern that would be considered by one skilled in the art to represent a compound possessing the same crystal form as the compound that provided the XRPD pattern of FIG. 1 or FIG. 2. It is well known and understood to those skilled in the art that the apparatus employed, humidity, temperature, orientation of the powder crystals, and other parameters involved in obtaining an X-ray powder diffraction pattern may cause some variability in the appearance, intensities, and positions of the lines in the diffraction pattern. Thus an X-ray powder diffraction pattern that is "substantially as shown in FIG. 1" or "substantially as shown in FIG. 2" may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining (e.g. by overlaying) if a sample of a crystalline compound has the same form as, or a different form from, a form disclosed herein by comparison of their XRPD patterns.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

A "therapeutically effective amount" of a compound, pharmaceutically acceptable salt or solvate thereof or pharmaceutical composition according to any embodiment described herein, is an amount sufficient to produce a selected effect on at least one symptom or parameter of a specific disease or disorder. The therapeutic effect may be objective (i.e., measurable by some test or marker) or subjective (i.e., subject gives an indication of or feels an effect or physician observes a change). The effect contemplated herein, includes both medical therapeutic and/or prophylactic treatment, as appropriate. The specific dose of a compound administered according to this disclosure to obtain therapeutic and/or prophylactic effects is determined by the particular circumstances surrounding the case, including, for example, the compound administered, the route of administration, the co-administration of other active ingredients, the condition being treated, the activity of the specific compound employed, the specific composition employed, the age, body weight, general health, sex and diet of the patient; the time of administration, route of administration, and rate of excretion of the specific compound employed and the duration of the treatment. The therapeutically effective amount administered will be determined by the physician in the light of the foregoing relevant circumstances and the exercise of sound medical judgment. A therapeutically effective amount of a compound, according to any embodiment described herein, is typically an amount such that when it is administered in a physiologically tolerable excipient composition, it is sufficient to achieve an effective systemic concentration or local concentration in the tissue.

Although the present invention has been described in considerable detail with reference to certain preferred embodiments thereof, other versions are possible. Therefore, the spirit and scope of the appended claims should not be limited to the description and the preferred versions contained within this specification. Various embodiments of the present invention will be illustrated with reference to the following non-limiting examples. The following examples are for illustrative purposes only and are not to be construed as limiting the invention in any manner.

As used herein the symbols and conventions used in these processes, schemes and examples are consistent with those used in the contemporary scientific literature, for example, the Journal of the American Chemical Society or the Journal of Biological Chemistry. Unless otherwise noted, all starting materials were obtained from commercial suppliers and used without further purification. Specifically, the following abbreviations may be used in the examples and throughout the specification:

Abbreviations

AcOH acetic acid
APCI Atmospheric Pressure Chemical Ionization
aq aqueous
$CH_3CN$ acetonitrile
$CH_3COOH$ acetic acid
$CH_3OH$ methanol
DCDMH 1,3-dichloro-5,5-dimethylhydantoin
DMAC dimethylacetamide
DMF N,N-dimethylformamide
DMPU 1,3-dimethyltetrahydropyrimidin-2(1H)-one
DMSO dimethyl sulfoxide
Et ethyl
EtOH ethanol
equiv equivalents
HCl hydrochloric acid
HRMS High Resolution Mass Spectrometry
iPr isopropyl
KOH potassium hydroxide
KOtButoxide potassium tert-butoxide
LiBr lithium bromide
Me methyl
2-MeTHF 2-methyl tetrahydrofuran
MHz megahertz
MIBK methyl isobutyl ketone
MS mass spectrometry
NaOH sodium hydroxide
$NEt_3$ triethylamine
$NH_4Cl$ ammonium chloride
NMR Nuclear Magnetic Resonance
TBAC tetrabutylammonium chloride
TBME tert-butyl methyl ether
tBu tert-butyl
tBuOK potassium tert-butoxide
TCCA trichloroisocyanuric acid
TEAC tetraethylammonium chloride

EXAMPLES

General Experimental Procedures. All reactions were performed under positive pressure of nitrogen in a Jacketed Laboratory Reactor equipped with overhead stirring and fitted with Teflon septa.

Materials: Commercial solvents and reagents were used as received.

Instrumentation:

Unless otherwise stated proton nuclear magnetic resonance spectra ($^1$H NMR) were recorded at 400 MHz at 25° C. Chemical shifts are expressed in parts per million (ppm, δ scale) downfield from tetramethylsilane and are referenced to residual proton in the NMR solvent. Data are represented as follows: chemical shift, multiplicity (s=singlet, d=doublet, sep=septet, m=multiplet and/or multiple resonances, br=broad), integration, coupling constant in Hertz, and assignment. Proton-decoupled carbon nuclear magnetic resonance spectra ($^{13}$C NMR) were recorded at 100 MHz at 25° C. Chemical shifts are expressed in parts per million (ppm, δ scale) downfield from tetramethylsilane and are referenced to the carbon resonances of the solvent. High-resolution mass spectrometry (HRMS) were obtained using an Orbitrap mass analyzer.

The X-ray powder diffraction (XRPD) data were acquired on a PANalytical X'Pert Pro powder diffractometer, model PW3050/60, using an X'Celerator detector. The acquisition conditions were: radiation: Cu Kα, generator tension: 45 kV, generator current: 40 mA, step size: 0.017 °2θ, time per step: 500 seconds, divergence slit type: fixed, divergence slit size: 0.4354°, measurement temperature: 20-25° C., goniometer radius: 240 mm. The sample was prepared by packing sample in a 0.9 mm capillary, or zero background silicone sample holder. Peak positions were obtained using PANalytical X'Pert Highscore Plus software. The margin of error is approximately ±0.1° 2θ for each of the peak assignments.

Example 1

Synthesis of (5E,7E)-2-methyl-8-phenylocta-5,7-dien-4-one, (compound of Formula (VIII))

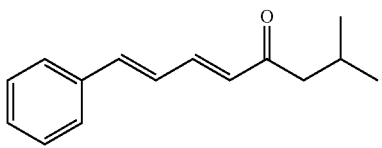

(VIII)

A solution of sodium hydroxide (11.4 g, 284 mmol, 1.5 equiv) in methanol (100 mL) was added dropwise over 1 hour to a stirred solution of cinnamaldehyde (compound of Formula (IX)) (25 g, 189 mmol, 1 equiv) and methyl isobutyl ketone (75 mL, 602 mmol, 3.2 equiv) at −5° C. Upon completion of the addition, the reaction mixture was stirred for 2 hours at 0° C. Toluene (250 mL) and water (125 mL) were then added directly to the reactor at 0° C. and the stirring biphasic mixture allowed to warm to 20° C. The aqueous layer was removed and the organic layer was washed with water (2×75 mL). The washed organic layer was then dried via azeotropic distillation under vacuum to a final solution volume of 75 mL or until analysis via Karl Fischer titration revealed water content less than 0.2%. The crude material was utilized in the next transformation without any further processing.

Example 2

Synthesis of (E)-di-tert-butyl 2-(7-methyl-5-oxo-1-phenyloct-1-en-3-yl)malonate, (compound of Formula VII in which R$_1$+R$_2$=tBu)

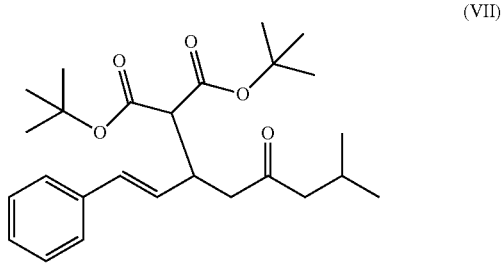 [SMILES: CC(C)CC(=O)CC(/C=C/c1ccccc1)C(C(=O)OC(C)(C)C)C(=O)OC(C)(C)C]

(VII)

The concentrated solution obtained in the previous step (example 1) was diluted with toluene such that the total volume of the solution was 175 mL. To the solution of (5E, 7E)-2-methyl-8-phenylocta-5,7-dien-4-one, (compound of Formula (VIII)) in toluene at 20° C. was then added di-tert-butyl malonate (40.3 mL, 180 mmol, 0.95 equiv), triethylamine (13.1 mL, 94.5 mmol, 0.5 equiv), and powdered lithium bromide (3.28 g, 37.8 mmol, 0.2 equiv). The heterogeneous reaction mixture was stirred for 2 hours at 20° C. Water (200 mL) was then charged directly to the stirring reaction mixture. The layers were allowed to separate and the aqueous layer discarded. The resulting product solution was utilized in the next transformation without any further processing. Alternatively, the di-tert-butyl malonate addition product (E)-di-tert-butyl 2-(7-methyl-5-oxo-1-phenyloct-1-en-3-yl)malonate (compound of Formula (VII)) could also be isolated via concentration of the toluene solution and crystallization from isopropyl alcohol/water (3:2) to provide (E)-di-tert-butyl 2-(7-methyl-5-oxo-1-phenyloct-1-en-3-yl)malonate (compound of Formula (VII)) as a light yellow solid.

$^1$H NMR (400 MHz, DMSO) δ 7.32-7.29 (m, 4H), 7.24-7.18 (m, 1H), 6.38 (d, 1H, J=16 Hz), 6.12 (dd, 1H, J=16, 8.4 Hz), 3.39 (d, 1H, J=8.4 Hz), 3.27-3.20 (m, 1H), 2.70 (dd, 1H, J=16.8, 9.2 Hz), 2.58 (dd, 1H, J=16.8, 4.4 Hz), 2.28 (d, 2H, J=7.2 Hz), 1.98 (sep, 1H, J=6.8 Hz), 1.39 (s, 9H), 1.33 (S, 9H), 0.81 (d, 3H, J=6.4 Hz), 0.80 (d, 3H, J=6.4 Hz).

$^{13}$C NMR (100 MHz, DMSO) δ 208.2 (C), 167.0 (C), 166.8 (C), 136.7 (C), 131.2 (CH), 129.1 (CH), 128.6 (CH), 127.3 (CH), 125.9 (CH), 81.2 (C), 80.9 (C), 56.8 (CH), 51.4 (CH$_2$), 45.0 (CH$_2$), 37.7 (CH), 27.5 (CH$_3$), 27.4 (CH$_3$), 23.9 (CH), 22.3 (CH$_3$), 22.2 (CH$_3$).

HRMS-APCI (m/z) [M+H]$^+$ calcd for C$_{26}$H$_{39}$O$_5$, 431.2792; found, 431.2754.

Example 3

Synthesis of (E)-diethyl 2-(7-methyl-5-oxo-1-phenyloct-1-en-3-yl)malonate, (compound of Formula VIIa)

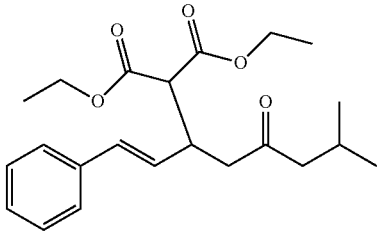

(VIIa)

A concentrated solution of (5E, 7E)-2-methyl-8-phenylocta-5,7-dien-4-one (about 7.6 moles) is diluted with toluene. To the solution of (5E, 7E)-2-methyl-8-phenylocta-5,7-dien-4-one, (compound of Formula (VIII)) in toluene at 20° C. is then added diethyl malonate (1.83 kg, 1.73 L, 1.5 equiv), triethylamine (1.15 kg, 1.58 L, 1.5 equiv), and powdered lithium bromide (131 g, 0.2 equiv). The heterogeneous reaction mixture is stirred at 35-40° C. for at least 8 hours. Water (8 L, 8 vols) is then charged directly to the stirring reaction mixture and stirred at 35° C. for 15-30 minutes. The layers are allowed to separate and the aqueous layer discarded. The resulting product solution is utilized in the next transformation without any further processing. Alternatively, the diethyl malonate addition product (E)-diethyl 2-(7-methyl-5-oxo-1-phenyloct-1-en-3-yl)malonate (compound of Formula (VIIa)) can also be isolated via concentration of the toluene solution and crystallization to provide (E)-diethyl 2-(7-methyl-5-oxo-1-phenyloct-1-en-3-yl)malonate (compound of Formula (VIIa)).

$^1$H NMR (700 MHz, DMSO) δ 7.30 (m, 2H), 7.30 (m, 5H0, 7.21 (m, 1H), 6.39 (d, 1H) J=15.8 Hz), 6.14 (dd, 1H, J=15.99 Hz, J=8.9 Hz), 4.12 (q, 2H, J=7.13 Hz), 4.06 (m, 2H), 3.68 (d, 1H, J=8.1 Hz), 3.33 (m, 1H), 2.73 (dd, 1H, J=16.9 Hz, J=9.0 Hz), 2.63 (m, 1H), 2.28 (d, 2H, 6.9 Hz), 1.98 (m, 1H, 6.7 Hz), 1.16 (t, 3H, J=7.1 Hz), 1.10 (t, 3H, J=7.0 Hz), 0.81 (d, 3H, J=6.6 Hz), 0.80 (d, 3H, J=6.7 Hz).

$^{13}$C NMR (176 MHz, DMSO) δ 208.1 (C), 167.7 (C), 167.6 (C), 136.6 (C), 131.4 (CH), 128.9 (CH), 127.4 (CH), 125.9 (CH), 61.0 (CH2), 60.8 (CH2), 55.0 (CH), 51.3 (CH2), 44.8 (CH2), 37.7 (CH), 23.8 (CH), 22.3 (CH3), 22.2 (CH3), 13.9 (CH3), 13.9 (CH3).

HRMS-APCI (m/z) [M+H]$^+$ calcd for $C_{22}H_{31}O_5$, 375.2166; found, 375.2158.

Example 4

Synthesis of (E)-2-(7-methyl-5-oxo-1-phenyloct-1-en-3-yl)malonic acid, (compound of Formula (VI))

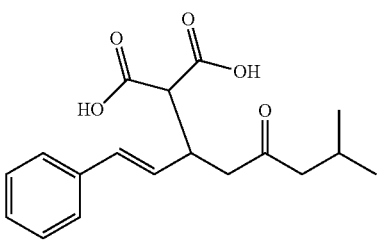

(VI)

Method A

The toluene solution of (E)-di-tert-butyl 2-(7-methyl-5-oxo-1-phenyloct-1-en-3-yl)malonate (compound of Formula (VII)) obtained in the previous step was diluted with acetic acid (50 mL) and added drop wise over 1 hour to a stirred solution consisting of acetic acid (100 mL) and concentrated aqueous hydrochloric acid (75 mL) at 60° C. Upon completion of the addition, the resulting solution was stirred for 4 hours at 60° C. The product mixture was allowed to cool over 30 minutes to 20° C. and water (200 mL) added. The two layers were stirred vigorously at 20° C. and then allowed to settle. The aqueous layer was then discarded and the toluene layer concentrated to dryness. To the resulting oil was added toluene (250 mL) and the solution heated to 60° C. with stirring. The warm toluene solution was then allowed to cool slowly over 1 hour to 20° C. at which point (E)-2-(7-methyl-5-oxo-1-phenyloct-1-en-3-yl)malonic acid (compound of Formula (VI)) precipitated from solution. The solid was then filtered and the wet cake washed with toluene (100 mL). The wet cake was then dried under vacuum at 30° C. for 12 hours to afford (E)-2-(7-methyl-5-oxo-1-phenyloct-1-en-3-yl)malonic acid (compound of Formula (VI)) as a white crystalline solid (37.3 g, 62% from cinnamaldehyde (compound of Formula (IX)).

Method B

A toluene solution of (E)-diethyl 2-(7-methyl-5-oxo-1-phenyloct-1-en-3-yl)malonate from example 3 (about 7.6 moles, compound of Formula (VIIa)) at 20-30° C. was charged with 6M aqueous sodium hydroxide (5.05 L, 4 equiv), toluene (0.5 L or 0.5 vols), and 200 proof ethanol (2 vols) and the contents were stirred for at least 4 h at T$_j$=20° C. Once complete, the temperature was adjusted to 35-50° C. and after stirring for at least 30 minutes agitation was stopped and the layers were separated. The aqueous layer was cooled to 0-5° C. and the pH was adjusted with conc. HCl to a pH of 0-1 (required 2.9 L or 4.7 equiv), while maintaining the temperature at 10° C. or less during the addition. Once the desired pH was reached the vessel was charged with TBME (3 L, 3 vols) and the biphasic mixture was warmed to 20-25° C. The mixture was stirred for 15-30 minutes and the layers were separated. To the organic layer was added toluene (7 L, 7 vols) and water (6 L, 6 vols) and the mixture was stirred for 15-30 minutes. The layers were separated and toluene was added to achieve a fill of 16-18 vols (3 L, 3 vols). The mixture was distilled down to about 9-9.5 vols using vacuum distillation, the temperature was adjusted to 40-45° C. and the mixture was seeded with 5 g of compound VI (0.2% w/w against theoretical yield). The mixture was stirred at 40-45° C. for 30-60 minutes. Once nucleation was observed the mixture was diluted to 12 volumes with toluene and held at 40-45° C. for at least 1 hour. The slurry was cooled to 10-20° C. at 0.5° C./min and held at 10-20° C. for at least 1 hour. The solid was isolated by filtration and the filter cake was washed with toluene (2×7 vols). The solid was dried at 25-35° C. overnight in a vacuum oven to afford (E)-2-(7-methyl-5-oxo-1-phenyloct-1-en-3-yl)malonic acid (compound of Formula (VI))

$^1$H NMR (400 MHz, DMSO) δ 12.78 (br s, 2H), 7.32-7.27 (m, 4H), 7.23-7.19 (m, 1H), 6.39 (d, 1H, J=16 Hz), 6.17 (dd, 1H, J=16, 8.4 Hz), 3.43 (d, 1H, J=8.4 Hz), 3.31-3.24 (m, 1H), 2.72 (dd, 1H, J=16.8, 8.8 Hz), 2.63 (dd, 1H, J=16.4, 4 Hz), 2.28 (d, 2H, J=7.2 Hz), 1.98 (sep, 1H, J=6.8 Hz), 0.81 (d, 3H, J=6.4 Hz), 0.80 (d, 3H, J=6.4 Hz).

$^{13}$C NMR (100 MHz, DMSO) δ 208.4 (C), 169.6 (C), 169.5 (C), 136.8 (C), 130.9 (CH), 129.6 (CH), 128.5 (CH), 127.3 (CH), 126.0 (CH), 55.7 (CH), 51.4 (CH$_2$), 45.1 (CH$_2$), 37.6 (CH), 23.9 (CH), 22.3 (CH$_3$), 22.2 (CH$_3$).

HRMS-APCI (m/z) [M+H]$^+$ calcd for C$_{18}$H$_{23}$O$_5$, 319.1540; found, 319.1528.

Example 5

Synthesis of (E)-2-isopropyl-5-styrylcyclohexane-1,3-dione, (compound of Formula (III))

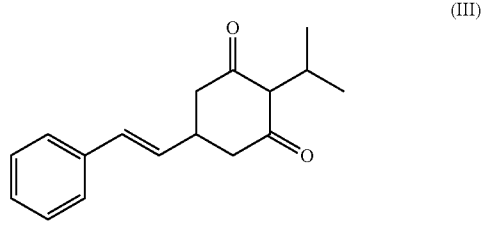 [SMILES: CC(C)C1C(=O)CC(/C=C/c2ccccc2)CC1=O]

(III)

Triethylamine (4.4 mL, 31.4 mmol, 0.25 equiv) was charged to a stirred slurry of (E)-2-(7-methyl-5-oxo-1-phenyloct-1-en-3-yl)malonic acid (compound of Formula (VI)) (40.0 g, 126 mmol, 1 equiv) in toluene (210 mL). The resulting mixture was heated to 110° C. and allowed to stir 2 hours. The reaction mixture containing the non-isolated intermediate (E)-7-methyl-5-oxo-3-styryloctanoic acid (compound of Formula V) was then allowed to cool to 20° C. and charged with methanol (120 mL) and concentrated aqueous hydrochloric acid (10.5 mL). The resulting solution was stirred for 4 hours at 60° C. The resulting mixture, containing the non-isolated intermediate (E)-methyl 7-methyl-5-oxo-3-styryloctanoate (compound of Formula (IVa)), was allowed to cool to 20° C. and washed with water (200 mL). The washed organic layer was then dried via vacuum distillation to a final solution volume of 120 mL. The solution of the methyl ester (E)-methyl 7-methyl-5-oxo-3-styryloctanoate (compound of Formula IVa) was then cooled to 0° C. A solution of potassium tert-butoxide (19.7 g, 176 mmol, 1.4 equiv) in 2-methyltetrahydrofuran (80 mL) was then added drop wise over 1 hour to the cooled solution of (E)-methyl 7-methyl-5-oxo-3-styryloctanoate (compound of Formula (IVa)). Upon completion of the addition, the reaction mixture was warmed over 30 minutes to 20° C. The warmed solution was stirred 1 hour at 20° C. The resulting product mixture was then charged with 1.0 M aqueous hydrochloric acid (180 mL) and the biphasic mixture stirred 10 minutes. The aqueous layer was then discarded and the organic layer washed with 10% aqueous sodium chloride (2×160 mL). To the solution of the (E)-2-isopropyl-5-styryl-cyclohexane-1,3-dione (compound of Formula (III)) was then added methylcyclohexane (400 mL) drop wise over 1 hour at which point the product began to precipitate out. The slurry was then filtered and the wet cake washed with methylcyclohexane (120 mL). The wet cake was then dried under vacuum at 30° C. for 12 hours to provide (E)-2-isopropyl-5-styrylcyclohexane-1,3-dione (compound of Formula (III)) as a white crystalline solid (25.3 g, 79% from (E)-2-(7-methyl-5-oxo-1-phenyloct-1-en-3-yl)malonic acid, (compound of Formula (VI)).

$^1$H NMR (400 MHz, DMSO) δ 10.33 (br s, 1H, OH), 7.39-7.37 (m, 2H), 7.34-7.29 (m, 2H), 7.24-7.20 (m, 1H), 6.43 (d, 1H, J=16 Hz), 6.27 (dd, 1H, J=16, 7.2 Hz), 3.08 (sep, 1H, J=7.2 Hz), 2.87-2.78 (m, 1H), 2.40 (br, 4H), 1.08 (d, 6H, J=7.2 Hz).

$^{13}$C NMR (100 MHz, DMSO) δ 136.8 (C), 132.5 (CH), 128.9 (CH), 128.6 (CH), 127.3 (CH), 126.0 (CH), 119.2 (C), 36.1 (CH), 22.6 (CH), 20.4 (CH$_3$), other carbons undergo enol tautomerization.

HRMS-APCI (m/z) [M+H]$^+$ calcd for C$_{17}$H$_{21}$O$_2$, 257.1536; found, 257.1519.

Example 6

Synthesis of (E)-2-chloro-2-isopropyl-5-styrylcyclohexane-1,3-dione, (compound of Formula (IIa))

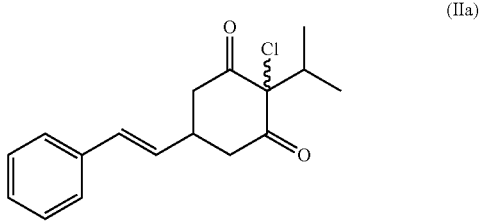

(IIa)

A 1-L jacketed laboratory reactor was charged with (E)-2-isopropyl-5-styrylcyclohexane-1,3-dione (compound of Formula (III)) (55 g, 215 mmol, 1 equiv) and methanol (495 mL) resulting in a heterogeneous suspension. The mixture was heated to an internal temperature of ~45-50° C. at which point a homogeneous solution was achieved. To this solution was charged solid 1,3-dichloro-5,5-dimethylhydantoin (23.3 g, 118 mmol, 0.55 equiv) sequentially, in five equal portions. The product solution was then cooled to 40° C. over 10 minutes and seeded with 146 mg of (E)-2-chloro-2-isopropyl-5-styrylcyclohexane-1,3-dione (compound of Formula (IIa)). The mixture was aged for 30 minutes then cooled to 23° C. over 60 minutes. Water (330 mL) was then added drop wise to the slurry over 1 hour and the mixture stirred 30 minutes at 20° C. The slurry was then filtered and the wet cake washed with 1:1 methanol/water (2×110 mL). The wet cake was then dried under vacuum at 45° C. for 12 hours to provide (E)-2-chloro-2-isopropyl-5-styrylcyclohexane-1,3-dione (compound of Formula (IIa)) as a white crystalline solid existing as a ~2:1 mixture of diastereomers (60.0 grams, 96%).

Isomer 1

¹H NMR (400 MHz, DMSO) δ 7.41-7.39 (m, 2H), 7.36-7.32 (m, 2H), 7.23-7.22 (m, 1H), 6.54 (d, 1H, J=16 Hz), 6.32 (dd, 1H, J=16, 7.2 Hz), 3.20-3.14 (m, 3H), 2.84-2.77 (m, 1H), 2.73-2.72 (m, 1H), 2.70-2.69 (m, 1H), 0.82 (d, 6H, J=6.8 Hz).

¹³C NMR (100 MHz, DMSO) δ 198.5 (C), 136.5 (C), 130.4 (CH), 129.9 (CH), 128.6 (CH), 127.5 (CH), 126.1 (CH), 94.6 (C), 43.4 (CH₂), 35.0 (CH), 32.8 (CH), 16.7 (CH₃).

Isomer 2

¹H NMR (400 MHz, DMSO) δ 7.33-7.28 (m, 4H), 7.25-7.21 (m, 2H), 6.35 (dd, 1H, J=16, 2 Hz), 6.03 (dd, 1H, J=16, 5.6 Hz), 3.48 (dd, 1H, J=14.8, 6 Hz), 3.24-3.18 (m, 1H), 3.10 (sep, 1H, J=6.4 Hz), 2.86 (dd, 1H, J=14.8, 3.6 Hz), 0.83 (d, 6H, J=6.4 Hz).

¹³C NMR (100 MHz, DMSO) δ 199.6 (C), 136.1 (C), 130.3 (CH), 130.1 (CH), 128.6 (CH), 127.7 (CH), 126.1 (CH), 94.5 (C), 42.2 (CH₂), 34.7 (CH), 30.9 (CH), 16.9 (CH₃).

HRMS-APCI (m/z) [M+H]⁺ calcd for $C_{17}H_{20}ClO_2$, 291.1146; found, 291.1132.

Example 7

Synthesis of (E)-2-isopropyl-5-styrylbenzene-1,3-diol, (compound of Formula (I))

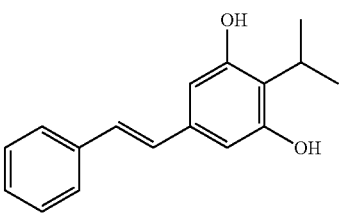

(I)

A jacketed laboratory reactor was charged with (E)-2-chloro-2-isopropyl-5-styrylcyclohexane-1,3-dione (compound of Formula (IIa)) (407 g, 1.4 mol, 1 equiv), tetraethylammonium chloride (464 g, 2.8 mol, 2 equiv), and acetonitrile (1.2 L). The mixture was heated to 75-80° C. for 6 hours. The product mixture was then cooled over 30 minutes to 20° C. and diluted with tert-butyl methyl ether (3.26 L). The resulting solution was washed four times with water (2 L each wash). The resulting solution was concentrated to a volume of ~610 ml. Acetic acid (815 ml) was charged and the solution was concentrated under reduced pressure to a volume of ~1.3 L. The resultant slurry was heated to 55° C. until homogeneous then cooled slowly to 35° C. over the course of 1 hour during which time product precipitation commenced. Methylcyclohexane (6.5 L) was added to the slurry over the course of 2 hours. Once the addition was complete, the mixture was further cooled to ~23° C. over one hour. The solids were filtered and washed twice with 6:1 methylcyclohexane/AcOH. The isolated solid was then dried under vacuum at 80° C. for 24 hours to provide (E)-2-isopropyl-5-styrylbenzene-1,3-diol (compound of Formula (I)) as a white crystalline solid (305 g, 86%).

¹H NMR (400 MHz, DMSO) δ 9.05 (s, 2H, OH), 7.58-7.55 (m, 2H), 7.37-7.33 (m, 2H), 7.27-7.22 (m, 1H), 7.00 (d, 1H, J=16.4 Hz), 6.87 (d, 1H, J=16.4 Hz), 6.47 (s, 2H), 3.43 (sep, 1H, J=7.2 Hz), 1.24 (d, 6H, J=7.2 Hz).

¹³C NMR (100 MHz, DMSO) δ 156.4 (C), 137.0 (C), 134.7 (C), 128.9 (CH), 128.7 (CH), 127.4 (CH), 126.7 (CH), 126.3 (CH), 120.1 (C), 105.1 (CH), 23.7 (CH), 20.6 (CH₃).

HRMS-APCI (m/z) [M+H]⁺ calcd for $C_{17}H_{19}O_2$, 255.1380; found, 255.1376.

The invention claimed is:

1. A process for the preparation of a compound of Formula (I) or a salt or solvate thereof

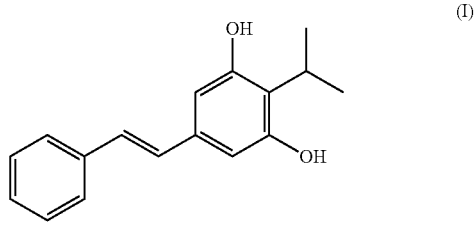 [SMILES: CC(C)c1c(O)cc(/C=C/c2ccccc2)cc1O]

(I)

comprising one or more of the process steps (a), (b) and (c) wherein:

(a) comprises (i) reaction of a compound of Formula (III) or a salt thereof

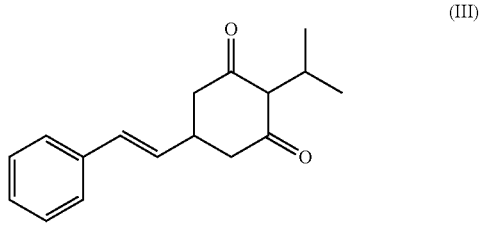 [SMILES: CC(C)C1C(=O)CC(/C=C/c2ccccc2)CC1=O]

(III)

to form a compound of Formula (II) or a salt thereof

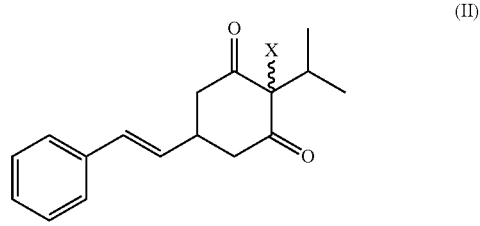

(II)

wherein X is Cl, Br, or I, and thereafter (ii) conversion of the compound of Formula (II) or a salt thereof into the compound of Formula (I) or a salt or solvate thereof;

(b) comprises conversion of a compound of Formula (VI) or a salt thereof

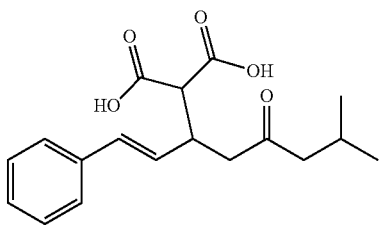

into a compound of Formula (III) or a salt thereof

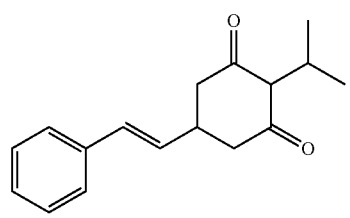

and thereafter conversion of the compound of Formula (III) or a salt thereof into a compound of Formula (I) or a salt or solvate thereof; and (c) comprises conversion of a compound of Formula (IX) or a salt thereof

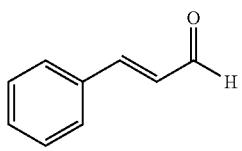

into a compound of Formula (VI) or a salt thereof

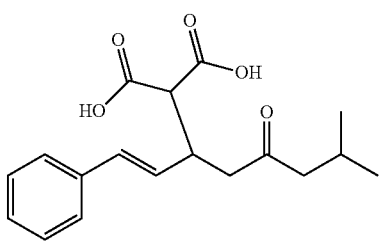

and thereafter conversion of the compound of Formula (VI) or a salt thereof into a compound of Formula (I) or a salt or solvate thereof.

2. The process according to claim 1 in which X is Cl and the process step (a) (i) is carried out using a chlorination reagent selected from the group consisting of 1,3-dichloro-5,5-dimethylhydantoin, N-chlorosuccinimide and trichloroisocyanuric acid.

3. The process according to claim 1 wherein the conversion step (a) (ii) is carried out in the presence of an additive reagent which is a quaternary ammonium salt.

4. The process according to claim 3 wherein the additive reagent is a quaternary ammonium chloride salt.

5. The process according to claim 4 wherein the quaternary ammonium chloride salt is selected from the group consisting of benzyltriethylammonium chloride, tetrabutylammonium chloride, tetraethylammonium chloride, and tetramethylammonium chloride.

6. The process according to claim 3 wherein the conversion is carried out in a solvent selected from the group consisting of acetonitrile, toluene, 2-methyl tetrahydrofuran, isopropyl acetate, acetone and methyl isobutyl ketone.

7. The process according to claim 1 in which process step (b) comprises a decarboxylation of the compound of Formula (VI) or a salt thereof to form the compound of Formula (V) or a salt thereof

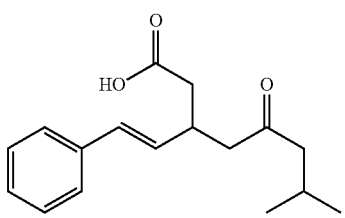

followed by esterification of the compound of Formula (V) or salt thereof to form the compound of Formula (IV) or a salt thereof

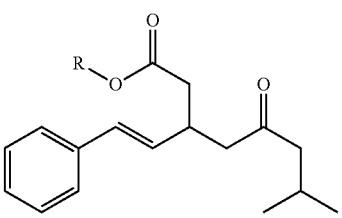

wherein R is $C_{1-4}$ alkyl; and thereafter cyclization of the compound of Formula (IV) or a salt thereof to form the compound of Formula (III) or a salt thereof.

8. The process according to claim 7 which comprises a decarboxylation in the presence of a base.

9. The process according to claim 8 wherein the base is triethylamine.

10. The process according to claim 7 wherein esterification is performed using methanol and hydrochloric acid.

11. The process according to claim 7 wherein cyclization is performed using potassium tert-butoxide.

12. The process according to claim 7 wherein the compound of Formula (III) or a salt thereof is acidified and isolated by precipitation with methylcyclohexane.

13. The process according to claim 1 in which process step (c) comprises the condensation of the compound of Formula (IX) or a salt thereof to form the compound of Formula (VIII) or a salt thereof

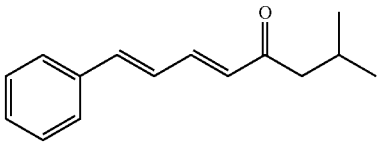

followed by addition of a malonic ester (R₁O(O)C—CH₂—C(O)OR₂) to form a compound of Formula (VII) or a salt thereof

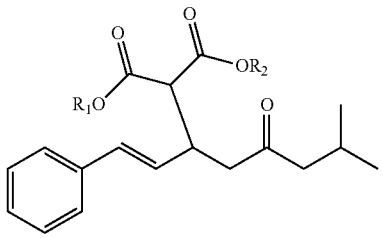

(VII)

wherein R₁ and R₂ are independently $C_{1-4}$ alkyl;

and thereafter hydrolysation of the compound of Formula (VII) or a salt thereof to form the compound of Formula (VI) or a salt thereof.

14. The process according to claim 13 wherein the condensation is performed using potassium or sodium hydroxide in methanol.

15. The process according to claim 13 wherein the malonic ester is diethyl malonate.

16. The process according to claim 1 in which step (a) (ii) further comprises the formation of an acetic acid solvate of the compound of Formula (I).

17. The process according to claim 1 wherein the process further comprises a step of recrystallization of the compound of Formula (I) or a salt thereof.

18. The process according to claim 17 wherein the recrystallization is carried out using methanol and water.

* * * * *